(12) United States Patent
Takuma et al.

(10) Patent No.: US 7,840,417 B2
(45) Date of Patent: Nov. 23, 2010

(54) MEDICAL INFORMATION PROVIDING APPARATUS, CONTROL METHOD, CONTROL PROGRAM, AND COMPUTER READABLE RECORDING MEDIUM RECORDED WITH CONTROL PROGRAM

(75) Inventors: Naoya Takuma, Tokyo (JP); Yasuo Shiga, Tokyo (JP); Noboru Saito, Tokyo (JP); Ayaki Miyaji, Tokyo (JP)

(73) Assignee: Care Net, Inc., Tokyo (JP)

( * ) Notice: Subject to any disclaimer, the term of this patent is extended or adjusted under 35 U.S.C. 154(b) by 1335 days.

(21) Appl. No.: 11/248,225

(22) Filed: Oct. 13, 2005

(65) Prior Publication Data

US 2007/0027713 A1 Feb. 1, 2007

(30) Foreign Application Priority Data

Jul. 27, 2005 (JP) .............................. 2005-217666

(51) Int. Cl.
*G06Q 10/00* (2006.01)
*G06F 19/00* (2006.01)

(52) U.S. Cl. .............................................. 705/2; 705/3
(58) Field of Classification Search ................. 705/2–3, 705/14
See application file for complete search history.

(56) References Cited

U.S. PATENT DOCUMENTS

| | | | |
|---|---|---|---|
| 2001/0032125 A1* | 10/2001 | Bhan et al. | 705/14 |
| 2002/0065683 A1* | 5/2002 | Pham et al. | 705/2 |
| 2004/0243437 A1* | 12/2004 | Grace et al. | 705/2 |

FOREIGN PATENT DOCUMENTS

| | | |
|---|---|---|
| JP | 2000112344 | 4/2000 |
| JP | 2004-038878 | 2/2004 |
| JP | 200438878 | 2/2004 |
| JP | 2004199217 | 7/2004 |
| JP | 2005198098 | 7/2005 |
| WO | WO2005/062223 | 7/2005 |

\* cited by examiner

*Primary Examiner*—Robert W Morgan
*Assistant Examiner*—Joseph Burgess
(74) *Attorney, Agent, or Firm*—Kenealy Vaidya LLP

(57) ABSTRACT

A medical information providing apparatus is provided which can increase the number of doctor side terminals to be destinations of program distribution, acquire market information extended in detail, positively creates circumstances in which a doctor desires to make contact with an MR, and promptly transmits information about a doctor who desires to make contact with the MR to him/her. A medical information providing apparatus can communicate with a doctor side terminal and a representative side terminal, in which the representative terminal can register doctor information on the medical information providing apparatus, and a medical information program is provided to registered doctor information. Before providing a medical information providing program, a basic questionnaire is done to efficiently provide the program, and a final questionnaire is done to obtain the effect to view the program after provided. Furthermore, a contact request questionnaire is done based on the results of these questionnaires. The doctor information and the answer for the basic questionnaire are collectively managed in an individual doctor information storing module for each doctor, and a reference individual doctor information storing module which discloses data to a representative is also formed.

10 Claims, 12 Drawing Sheets

F I G. 1
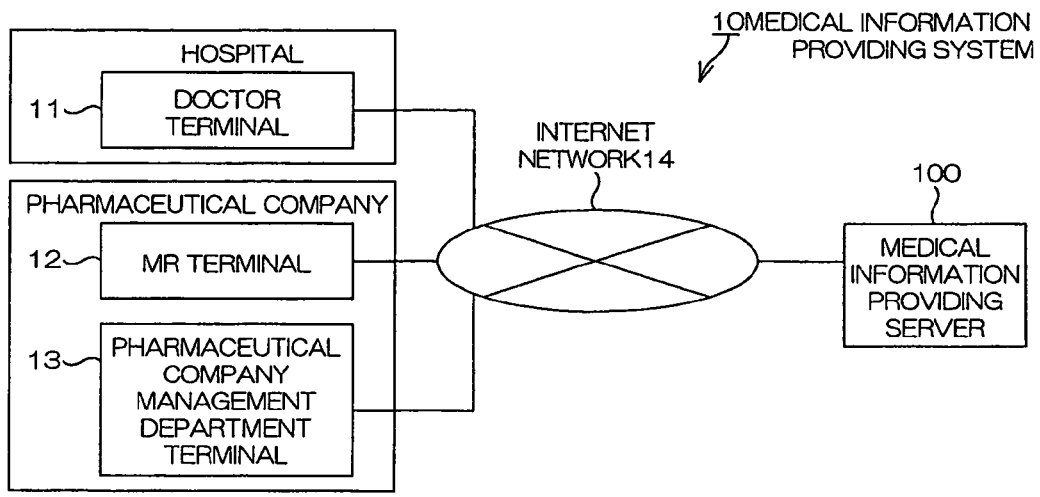
F I G. 2
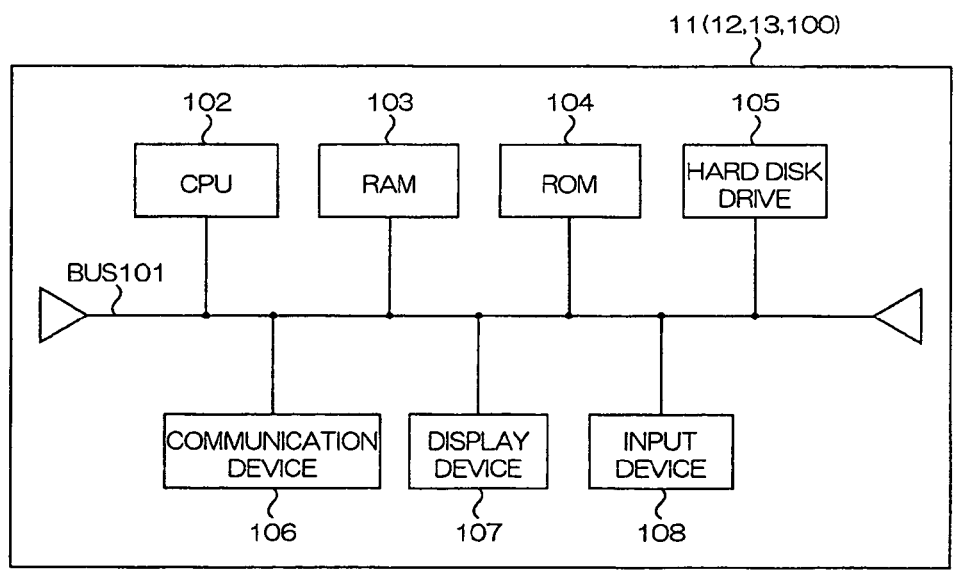

FIG.4

(KONO TARO) DOCTOR SPECIFIC FILE 121

| DOCTOR'S BASIC INFORMATION | | | | | |
|---|---|---|---|---|---|
| DOCTOR'S NAME | KONO TARO | ADDRESS | | | |
| OFFICE FACILITY | OTSUKAWA HOSPITAL | NUMBER OF BEDS | | | |
| CLINICAL DEPARTMENT | INTERNAL MEDICINE | POST | | | |
| URL WITH IDENTIFICATION SYMBOL | ... | | | | |
| MAIL ADDRESS | ... | | | | |
| PROPRIETY OF MAIL ADDRESS | CORRECT /INCORRECT | | | | |
| DISCLOSURE OF PROGRAM VIEWING RESULT TO PHARMACEUTICAL COMPANY | | YES/NO | | | |
| PROGRAM VIEWING HISTORY | YES/NO | | | | |
| VIEWING REJECTED PROGRAM | ○○ PROGRAM | ×× PROGRAM | △△ PROGRAM | □□ PROGRAM | |
| PHARMACEUTICAL COMPANY INFORMATION ABOUT MR IN CHARGE | | | | | |
| BRANCH | TOKYO OFFICE | | | | |
| DEPARTMENT | HOSPITAL DEPARTMENT | | | | |
| MR IN CHARGE | HEIYAMA SABURO | | | | |
| PROBING QUESTIONNAIRE RESULT | | | | | |
| NUMBER OF PATIENTS (INSOMNIA PATIENTS IN CHARGE) | | ···PERSONS | | | |
| RECOGNITION MEDICINES (DO YOU KNOW SLEEPING PILL A?) | | YES/NO | | | |
| USE CIRCUMSTANCES (DEGREE OF PRESCRIBING SLEEPING PILL A) | | ···BOXES | | | |
| NUMBER OF SPECIFIC DISEASE PATIENTS (HYPERTENSION PATIENTS) | | ···PERSONS | | | |
| CLOSING QUESTIONNAIRE RESULT | | | | | |
| WHEN SLEEPING PILL A HAS BEEN PRESCRIBED | | | | | |
| REFERENCE DEGREES OF PROGRAMS | | | | | |
| REASON FOR REFERENCE DEGREES | | | | | |
| NEW FORMULA/INTENTION TO ADOPT | | YES/NO | | | |
| NEW FORMULA/NUMBER OF ADOPTIONS | | ···BOXES | | | |
| NEW FORMULA/REASON FOR ADOPTION, COMMENTS ON SLEEPING PILL A | | | | | |
| NUMBER OF VISITS BY MR | | ···TIMES | | | |
| WHEN SLEEPING PILL A HAS NEVER BEEN PRESCRIBED | | | | | |
| REFERENCE DEGREES OF PROGRAMS | | | | | |
| REASON FOR REFERENCE DEGREES | | | | | |
| INTENTION TO INCREASE THE FORMULA | | YES/NO | | | |
| NUMBER OF THE FORMULA INCREASED | | ···BOXES | | | |
| REASON FOR AN INCREASE IN THE FORMULA, COMMENTS ON SLEEPING PILL A | | | | | |
| NUMBER OF VISITS BY MR | | ···TIMES | | | |
| REQUEST FOR MR'S CONTACT | | | | | |
| WOULD LIKE AN MR TO VISIT | | YES/NO | | | |
| WOULD LIKE MATERIALS TO BE SENT | | YES/NO | | | |
| WOULD LIKE TO HAVE DETAILING | | YES/NO | | | |

F I G. 5

PROGRAM INFORMATION FILE 124

| PROGRAM NAME | SLEEPING PILLS | CLINICAL DEPARTMENT | INTERNAL MEDICINE |
|---|---|---|---|
| PROGRAM CONTENTS | | | |
| 1.OPENING CONTENTS (HISTORY OF SLEEPING PILLS) ||||
| 2.SLEEPING PILLS TO BE SOUGHT ||||
| 3.IMPORTANCE OF INSOMNIA TREATMENT ||||
| 4.GUIDELINE FOR SLEEPING PILLS AND SLEEPING PILL A ||||
| 5.HYPERTENSION AND INSOMNIA ||||
| 6.TREATMENT OF TRANSIENT AND SHORT TERM INSOMNIA ||||

F I G. 6

HOSPITAL AND REPRESENTATIVE LIST TABLE 132

| MUNICIPALITIES | HOSPITAL NAME | CLINICAL DEPARTMENT | BRANCH | DEPARTMENT | MR IN CHARGE |
|---|---|---|---|---|---|
| TOKYO | HOSPITAL A | INTERNAL MEDICINE | TOKYO OFFICE | HOSPITAL DEPARTMENT | C |
| | | SURGERY | TOKYO OFFICE | HOSPITAL DEPARTMENT | C |

F I G. 7

PROBING QUESTIONNAIRE FILE 133

| |
|---|
| NUMBER OF PATIENTS (HOW MANY INSOMNIA PATIENTS DO YOU CARE?) |
| RECOGNITION MEDICINES (DO YOU KNOW SLEEPING PILL A?) |
| USE CIRCUMSTANCES (HOW MANY TIMES DO YOU PRESCRIBE SLEEPING PILL A?) |
| NUMBER OF SPECIFIC DISEASE PATIENTS (HOW MANY HYPERTENSION PATIENTS DO YOU CARE?) |

FIG. 8

PROGRAM PROVIDING ORDER FILE 135

| PROGRAM PROVIDING PATTERN 1 | (PROGRAM IS DISTRIBUTED, TEN OR MORE HYPERTENSION PATIENTS/MONTH, PRESCRIBES SLEEPING PILL A) |
|---|---|
| | PROVIDING ORDER(6→3→4→5→2→1) |
| PROGRAM PROVIDING PATTERN 2 | (PROGRAM IS DISTRIBUTED, TEN OR MORE HYPERTENSION PATIENTS/MONTH, NEVER PRESCRIBES SLEEPING PILL A) |
| | PROVIDING ORDER(6→2→3→4→5→1) |
| PROGRAM PROVIDING PATTERN 3 | (PROGRAM IS DISTRIBUTED, LESS THAN TEN HYPERTENSION PATIENTS/MONTH, PRESCRIBES SLEEPING PILL A) |
| | PROVIDING ORDER(6→3→4→5→2→1) |
| PROGRAM PROVIDING PATTERN 4 | (PROGRAM IS DISTRIBUTED, LESS THAN TEN HYPERTENSION PATIENTS/MONTH, NEVER PRESCRIBES SLEEPING PILL A) |
| | PROVIDING ORDER(6→2→3→4→5→1) |
| PROGRAM PROVIDING PATTERN 5 | (PROGRAM IS FIRST DISTRIBUTED, TEN OR MORE HYPERTENSION PATIENTS/MONTH, PRESCRIBES SLEEPING PILL A) |
| | PROVIDING ORDER(6→3→4→5→2) |
| PROGRAM PROVIDING PATTERN 6 | (PROGRAM IS FIRST DISTRIBUTED, TEN OR MORE HYPERTENSION PATIENTS/MONTH, NEVER PRESCRIBES SLEEPING PILL A) |
| | PROVIDING ORDER(6→2→3→4→5) |
| PROGRAM PROVIDING PATTERN 7 | (PROGRAM IS FIRST DISTRIBUTED, LESS THAN TEN HYPERTENSION PATIENTS/MONTH, PRESCRIBES SLEEPING PILL A) |
| | PROVIDING ORDER(6→3→4→5→2) |
| PROGRAM PROVIDING PATTERN 8 | (PROGRAM IS FIRST DISTRIBUTED, LESS THAN TEN HYPERTENSION PATIENTS/MONTH, NEVER PRESCRIBES SLEEPING PILL A) |
| | PROVIDING ORDER(6→2→3→4→5) |

FIG. 9

CLOSING QUESTIONNAIRE FILE 142

| CLOSING QUESTIONNAIRE FOR DOCTOR HAVING PRESCRIBED THE MEDICINE |
|---|
| (1) REFERENCE DEGREES OF PROGRAMS |
| (2) REASON FOR REFERENCE DEGREES |
| (3) NEW FORMULA/INTENTION TO ADOPT |
| (4) NEW FORMULA/NUMBER OF ADOPTIONS |
| (5) NEW FORMULA/REASON FOR ADOPTION, COMMENTS ON SLEEPING PILL A |
| (6) NUMBER OF VISITS BY MR |
| CLOSING QUESTIONNAIRE FOR DOCTOR HAVING NEVER PRESCRIBED THE MEDICINE |
| (1) REFERENCE DEGREES OF PROGRAMS |
| (2) REASON FOR REFERENCE DEGREES |
| (3) INTENTION TO INCREASE THE FORMULA |
| (4) NUMBER OF THE FORMULA INCREASED |
| (5) REASON FOR AN INCREASE IN THE FORMULA, COMMENTS ON SLEEPING PILL A |
| (6) NUMBER OF VISITS BY MR |

FIG.10

MR CONTACT REQUEST QUESTIONNAIRE FILE 145

| TYPES OF CONTACT QUESTIONNAIRES |
|---|
| ①WOULD YOU LIKE AN MR TO VISIT YOU? |
| ②WOULD YOU LIKE TO HAVE MATERIALS SENT? |
| ③WOULD YOU LIKE TO HOLD A BRIEFING SESSION AT MEDICAL DEPARTMENT? |

| REQUEST PATTERN 1 | |
|---|---|
| (CONDITIONS) | |
| IN PROBING QUESTIONNAIRE, TEN OR MORE PATIENTS | |
| IN PROBING QUESTIONNAIRE, ONE OR MORE SPECIFIC DISEASE PATIENTS | |
| IN CLOSING QUESTIONNAIRE, INTENTION TO ADOPT IS SHOWN (NUMBER OF ADOPTIONS (ONE OR MORE BOXES) OR INTENTION TO INCREASE) | |
| (QUESTIONNAIRE DESCRIPTIONS) | |
| DISPLAY①,②,AND③ | |

| REQUEST PATTERN 2 | |
|---|---|
| (CONDITIONS) | |
| IN PROBING QUESTIONNAIRE, 30 OR MORE PATIENTS | |
| IN PROBING QUESTIONNAIRE, TEN OR MORE SPECIFIC DISEASE PATIENTS | |
| IN CLOSING QUESTIONNAIRE, INTENTION TO INCREASE THREE OR MORE BOXES | |
| (QUESTIONNAIRE DESCRIPTIONS) | |
| DISPLAY ONLY① | |

| REQUEST PATTERN 3 | |
|---|---|
| (CONDITIONS) | |
| FACILITY TYPE INPUTTED IS A UNIVERSITY HOSPITAL OR A HOSPITAL HAVING 100 OR MORE BEDS WHEN THE DOCTOR REGISTERED | |
| (QUESTIONNAIRE DESCRIPTIONS) | |
| DISPLAY ONLY③ | |

| REQUEST PATTERN 4 | |
|---|---|
| (CONDITIONS) | |
| IN PROBING QUESTIONNAIRE, ONE OR MORE PATIENTS, ONE OR MORE BOXES ADOPTED | |
| IN PROBING QUESTIONNAIRE, ONE OR MORE SPECIFIC DISEASE PATIENTS | |
| IN CLOSING QUESTIONNAIRE, ONE OR MORE BOXES ADOPTED | |
| QUESTIONNAIRE DESCRIPTIONS) | |
| DISPLAY ONLY② | |

FIG. 11

(KONO TARO) REFERENCE DOCTOR SPECIFIC FILE 149
(IN THE CASE WHERE ALL ITEMS ARE NOT DISCLOSED)

| DOCTOR'S BASIC INFORMATION | | | | | |
|---|---|---|---|---|---|
| DOCTOR'S NAME | KONO TARO | ADDRESS | | | |
| OFFICE FACILITY | OTSUKAWA HOSPITAL | NUMBER OF BEDS | | | |
| CLINICAL DEPARTMENT | INTERNAL MEDICINE | POST | | | |
| URL WITH IDENTIFICATION SYMBOL | | ... | | | |
| MAIL ADDRESS | | ... | | | |
| PROPRIETY OF MAIL ADDRESS | | CORRECT /INCORRECT | | | |
| DISCLOSURE OF PROGRAM VIEWING RESULT TO PHARMACEUTICAL COMPANY | | YES/NO | | | |
| PROGRAM VIEWING HISTORY | | YES/NO | | | |
| VIEWING REJECTED PROGRAM | | NOT DISCLOSED | NOT DISCLOSED | NOT DISCLOSED | NOT DISCLOSED |
| PHARMACEUTICAL COMPANY INFORMATION ABOUT MR IN CHARGE | | | | | |
| BRANCH | TOKYO OFFICE | | | | |
| DEPARTMENT | HOSPITAL DEPARTMENT | | | | |
| MR IN CHARGE | HEIYAMA SABURO | | | | |
| PROBING QUESTIONNAIRE RESULT | | | | | |
| NUMBER OF PATIENTS (INSOMNIA PATIENTS IN CHARGE) | | NOT DISCLOSED | | | |
| RECOGNITION MEDICINES (DO YOU KNOW SLEEPING PILL A?) | | NOT DISCLOSED | | | |
| USE CIRCUMSTANCES (DEGREE OF PRESCRIBING SLEEPING PILL A) | | NOT DISCLOSED | | | |
| NUMBER OF SPECIFIC DISEASE PATIENTS (HYPERTENSION PATIENTS) | | NOT DISCLOSED | | | |
| CLOSING QUESTIONNAIRE RESULT | | | | | |
| WHEN SLEEPING PILL A HAS BEEN PRESCRIBED | | | | | |
| REFERENCE DEGREES OF PROGRAMS | | NOT DISCLOSED | | | |
| REASON FOR REFERENCE DEGREES | | NOT DISCLOSED | | | |
| NEW FORMULA/INTENTION TO ADOPT | | NOT DISCLOSED | | | |
| NEW FORMULA/NUMBER OF ADOPTIONS | | NOT DISCLOSED | | | |
| NEW FORMULA/REASON FOR ADOPTION, COMMENTS ON SLEEPING PILL A | | NOT DISCLOSED | | | |
| NUMBER OF VISITS BY MR | | NOT DISCLOSED | | | |
| WHEN SLEEPING PILL A HAS NEVER BEEN PRESCRIBED | | | | | |
| REFERENCE DEGREES OF PROGRAMS | | NOT DISCLOSED | | | |
| REASON FOR REFERENCE DEGREES | | NOT DISCLOSED | | | |
| INTENTION TO INCREASE THE FORMULA | | NOT DISCLOSED | | | |
| NUMBER OF THE FORMULA INCREASED | | NOT DISCLOSED | | | |
| REASON FOR AN INCREASE IN THE FORMULA, COMMENTS ON SLEEPING PILL A | | NOT DISCLOSED | | | |
| NUMBER OF VISITS BY MR | | NOT DISCLOSED | | | |
| REQUEST FOR MR'S CONTACT | | | | | |
| WOULD LIKE AN MR TO VISIT | | YES/NO | | | |
| WOULD LIKE MATERIALS TO BE SENT | | YES/NO | | | |
| WOULD LIKE TO HAVE DETAILING | | YES/NO | | | |

FIG.12

MR DAILY REPORT
(IN THE CASE WHERE ALL ITEMS ARE NOT DISCLOSED)

| DOCTOR'S BASIC INFORMATION | | | |
|---|---|---|---|
| DOCTOR'S NAME | KONO TARO | ADDRESS | |
| OFFICE FACILITY | OTSUKAWA HOSPITAL | NUMBER OF BEDS | |
| CLINICAL DEPARTMENT | INTERNAL MEDICINE | POST | |
| URL WITH IDENTIFICATION SYMBOL | | ... | |
| MAIL ADDRESS | | ... | |
| PROPRIETY OF MAIL ADDRESS | | CORRECT/INCORRECT | |
| DISCLOSURE OF PROGRAM VIEWING RESULT TO PHARMACEUTICAL COMPANY | | YES/NO | |
| PROGRAM VIEWING HISTORY | | YES/NO | |
| VIEWING REJECTED PROGRAM | NOT DISCLOSED | NOT DISCLOSED | NOT DISCLOSED | NOT DISCLOSED |

| PHARMACEUTICAL COMPANY INFORMATION ABOUT MR IN CHARGE | |
|---|---|
| BRANCH | TOKYO OFFICE |
| DEPARTMENT | HOSPITAL DEPARTMENT |
| MR IN CHARGE | HEIYAMA SABURO |

| PROBING QUESTIONNAIRE RESULT | |
|---|---|
| NUMBER OF PATIENTS (INSOMNIA PATIENTS IN CHARGE) | NOT DISCLOSED |
| RECOGNITION MEDICINES (DO YOU KNOW SLEEPING PILL A?) | NOT DISCLOSED |
| USE CIRCUMSTANCES (DEGREE OF PRESCRIBING SLEEPING PILL A) | NOT DISCLOSED |
| NUMBER OF SPECIFIC DISEASE PATIENTS (HYPERTENSION PATIENTS) | NOT DISCLOSED |

| CLOSING QUESTIONNAIRE RESULT | |
|---|---|
| WHEN SLEEPING PILL A HAS BEEN PRESCRIBED | |
| REFERENCE DEGREES OF PROGRAMS | NOT DISCLOSED |
| REASON FOR REFERENCE DEGREES | NOT DISCLOSED |
| NEW FORMULA/INTENTION TO ADOPT | NOT DISCLOSED |
| NEW FORMULA/NUMBER OF ADOPTIONS | NOT DISCLOSED |
| NEW FORMULA/REASON FOR ADOPTION. COMMENTS ON SLEEPING PILL A | NOT DISCLOSED |
| NUMBER OF VISITS BY MR | NOT DISCLOSED |
| WHEN SLEEPING PILL A HAS NEVER BEEN PRESCRIBED | |
| REFERENCE DEGREES OF PROGRAMS | NOT DISCLOSED |
| REASON FOR REFERENCE DEGREES | NOT DISCLOSED |
| INTENTION TO INCREASE THE FORMULA | NOT DISCLOSED |
| NUMBER OF THE FORMULA INCREASED | NOT DISCLOSED |
| REASON FOR AN INCREASE IN THE FORMULA. COMMENTS ON SLEEPING PILL A | NOT DISCLOSED |
| NUMBER OF VISITS BY MR | NOT DISCLOSED |

| REQUEST FOR MR'S CONTACT | |
|---|---|
| WOULD LIKE AN MR TO VISIT | YES/NO |
| WOULD LIKE MATERIALS TO BE SENT | YES/NO |
| WOULD LIKE TO HAVE DETAILING | YES/NO |

| REQUEST FOR MR'S CONTACT | | |
|---|---|---|
| VISIT DAY | DESCRIPTION | PRESCRIPTION |
| JANUARY 7 2005 | NEW YEAR GREETING | PRESCRIBED ONE FORMULA |

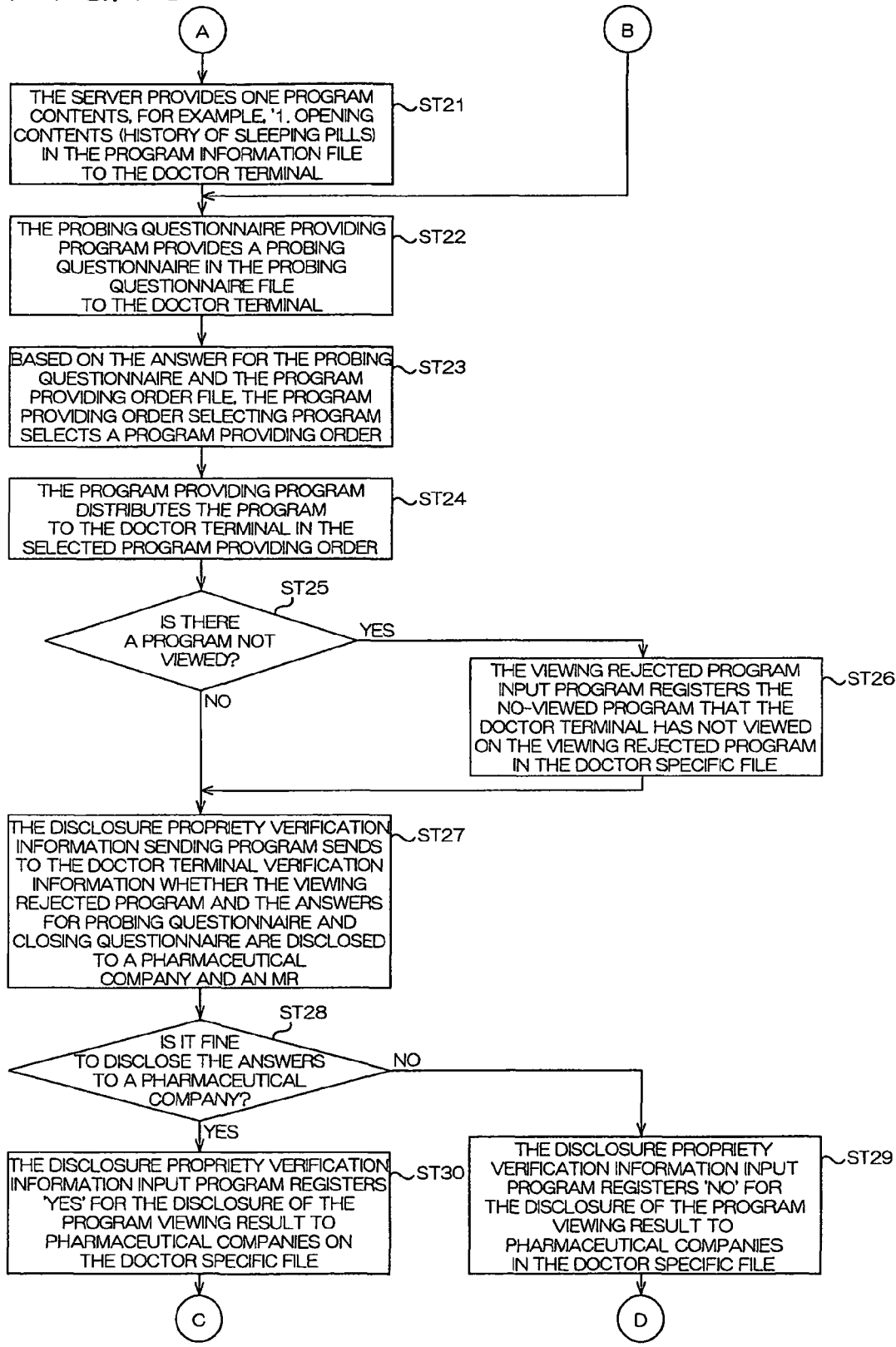

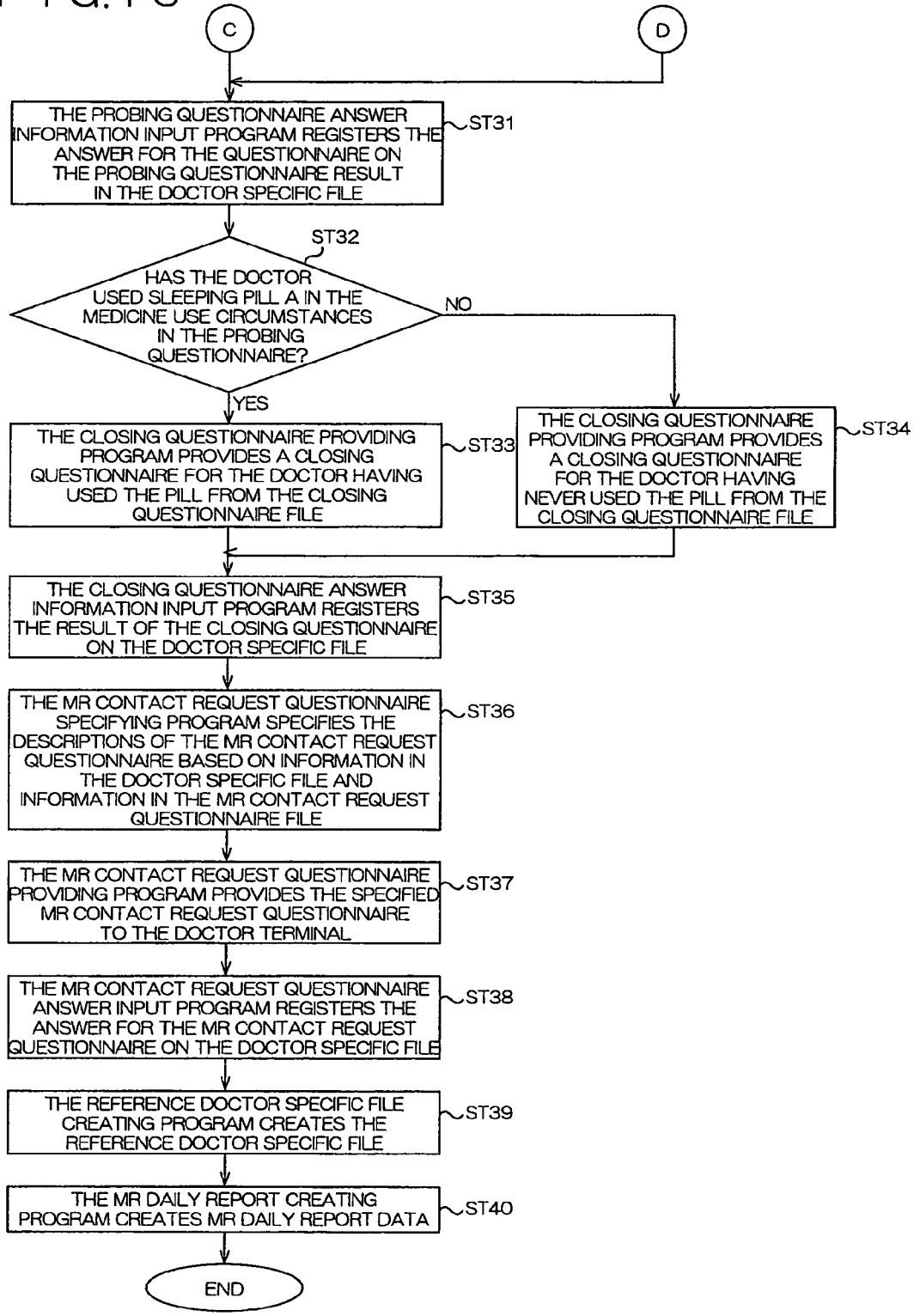

_US 7,840,417 B2_

MEDICAL INFORMATION PROVIDING APPARATUS, CONTROL METHOD, CONTROL PROGRAM, AND COMPUTER READABLE RECORDING MEDIUM RECORDED WITH CONTROL PROGRAM

This application claims the priorities benefit under 35 U.S.C. §119 of Japanese Patent Application No. 2005-217666 filed on Jul. 27, 2005, which is hereby incorporated in its entirety by reference.

BACKGROUND OF THE INVENTION

1. Field of the Invention

The present invention relates to a medical information providing apparatus, a control method of the medical information providing apparatus, a control program of the medical information providing apparatus, and a computer readable recording medium recorded with the control program of the medical information providing apparatus, which provide medical information for medical information representatives (hereinafter, it is abbreviated to 'MR') and for pharmaceutical companies that employ MRs, for example.

2. Description of the Related Art

Traditionally, there is an information providing system which distributes pharmaceutical information programs that suit for doctors in hospitals through a network of the Internet, acquires questionnaires, acquires information about medicines that doctors prescribe, and feeds it back to pharmaceutical companies (for example, see Patent Reference 1). Patent Reference 1: JP-A-2004-38878.

SUMMARY OF THE INVENTION

However, such the system described in Patent Reference 1 is aimed for doctors who positively register their addresses on the system. Furthermore, since the above pharmaceutical information program is distributed only to terminals of these doctors, market information about medicines obtained from the questionnaires is insufficient, leading to a problem that pharmaceutical companies have a difficulty grasping market circumstances.

On the other hand, an administrator who manages the system has a problem that when the administrator increases doctors who receive the program on the administrator's own act, it results in cost increase.

Then, a first aspect of the invention is to provide a device, method or system that increases the number of doctor side terminals to be destinations of program distribution with substantially no cost increase.

Furthermore, Patent Reference 1 is the system which allows pharmaceutical companies to use the questionnaire results from doctors for market strategies. However, the system of the Reference has a principal object that persistently provides pharmaceutical information programs for doctors, and the questionnaires give importance to a grasp of doctor's orientations for viewing the programs.

Therefore, information about a market for, doctor's medicine prescription is insufficient, leading to a problem that pharmaceutical companies cannot obtain detailed information about the market.

Then, another aspect of the invention is to provide a device, method or system that acquires market information that is extended in detail to doctor's personal level from questionnaire answers, and provides it for pharmaceutical companies and MRs.

Moreover, in Patent Reference 1, an MR can provide medical information without making contact with a doctor in his/her charge. However, on the other hand, since the MR is not encouraged to make contact with doctors, there is a problem that communications are not enough between the MR and doctors.

In reverse, there is a problem that when an MR visits a doctor and the doctor is not in circumstances to be able to listen to the MR, it produces no effect but backfires.

Then, another aspect of the invention is to provide a device, method or system that positively produces circumstances in which a doctor wants to make contact with an MR as well as to promptly inform an MR or a pharmaceutical company of information about a doctor who wants to have such contact.

According to a first aspect of the invention, a medical information providing apparatus can be provided which is arranged to be able to communicate with a doctor side terminal manipulated by a doctor and a representative side terminal manipulated by a medical information representative who provides medical information to the doctor, the medical information providing apparatus including: an individual doctor information storing module which stores to each doctor specific information including communication address information about the doctor side terminal specific to a doctor, doctor specialization information, and representative information, the information being inputted from the representative side terminal; an access information creating and input module which adds identification information varied for each doctor to information that permits the doctor side terminal to make access to the medical information providing apparatus, creates access information containing identification information, and enters the created access information containing identification information to the individual doctor information storing module; a medical information program storing module which classifies a medical information program formed of multiple programs to be provided to the doctor side terminal into each item of the doctor specialization information for storage; a medical information selecting module which selects the medical information program based on the doctor specialization information; a program guide information creating and sending module which creates and sends program providing guide information that acquires consent to send the selected medical information program based on the communication address information in the individual doctor information storing module and the access information containing identification information; a doctor specifying module which specifies the relevant individual doctor information storing module from the sent identification information when the access information containing identification information added to the program guide information is sent from the doctor side terminal to the medical information providing apparatus; a basic questionnaire information storing module which stores basic questionnaire information that grasps doctor's general orientation circumstances about doctor's prescription; a basic questionnaire information providing module which provides basic questionnaire information in the basic questionnaire information storing module to the doctor side terminal; a program providing order information storing module which stores multiple items of program providing order information that decide a providing order of multiple programs of the medical information program; a program providing order selecting module which selects a program providing order based at least on an answer for the basic questionnaire information provided to the doctor side terminal and the program providing order information; a program providing module which provides a program to the doctor side terminal based on program providing order information selected by the program providing order selecting module; a basic questionnaire answer information input module which enters an answer for the basic questionnaire information from the doctor side terminal to the individual doctor information storing module; a final questionnaire information storing module which stores final questionnaire information for grasping change in orientation about doctor's prescription after viewing the program; a final questionnaire information providing module which provides final questionnaire information in the final questionnaire information storing module to the doctor side terminal; a final questionnaire answer information input module which enters an answer for the final questionnaire information from the doctor side terminal to the individual doctor information storing module; a contact request questionnaire information storing module which stores multiple questionnaires as a contact request questionnaire on the medical information representative making contact with the doctor; a contact request questionnaire information specifying module which specifies a description of a questionnaire on the medical information representative making contact with the doctor based at least on an answer for the basic questionnaire information in the individual doctor information storing module and an answer for the final questionnaire information; a contact request questionnaire information providing module which provides to the doctor side terminal a type of contact request questionnaire information specified by the contact request questionnaire information specifying module; a contact request questionnaire answer input module which enters an answer for the contact request questionnaire from the doctor side terminal to the individual doctor information storing module; and a reference individual doctor information creating and input module which creates information in the individual doctor information storing module as reference individual doctor information for a pharmaceutical company and the medical information representative, and enters it to a reference individual doctor information storing module.

According to the configuration, the medical information providing apparatus has the individual doctor information storing module which stores to each doctor specific information including communication address information about the doctor side terminal specific to a doctor, doctor specialization information, and representative information, the information being inputted from the representative side terminal.

Therefore, it is configured that when the medical information representative positively offers doctor specific information about a doctor who the MR knows, the medical information providing apparatus positively accepts doctor specific information.

Thus, an administrator of the medical information providing apparatus can increase the number of new registered doctor side terminals by the medical information representative without looking for new doctor side terminals to be destinations of medical information programs at cost.

Furthermore, the program providing module can be configured to provide the medical information program to the doctor side terminal. Thus, the medical information providing apparatus can provide the program to a larger number of doctor side terminals.

Accordingly, the medical information providing apparatus can increase the number of doctor side terminals to be the destinations of program distribution with no cost increase.

Moreover, in accordance with an embodiment of the invention, a medical information program storing module can be provided which classifies a medical information program formed of multiple programs to be provided to the doctor side terminal into each item of the doctor specialization information for storage; and a medical information selecting module can be provided which selects the medical information program based on the doctor specialization information.

Therefore, the medical information program suited for the doctor's specialty of the registered doctor side terminal can be provided to the doctor side terminal, and the program fit to the doctor's orientation can be provided efficiently.

Besides, the configuration has the access information creating and input module which adds identification information varied for each doctor to information that permits the doctor side terminal to make access to the medical information providing apparatus, creates access information containing identification information, and enters the created access information containing identification information to the individual doctor information storing module; the program guide information creating and sending module which creates and sends program providing guide information for acquiring consent to send the selected medical information program based on the communication address information in the individual doctor information storing module and the access information containing identification information; and the doctor specifying module which specifies the relevant individual doctor information storing module from the sent identification information when the access information containing identification information added to the program guide information is sent from the doctor side terminal to the medical information providing apparatus.

Thus, when the doctor who has received program guide information desires to view a program, the doctor only clicks access information such as a URL with identification information on the screen of the doctor side terminal, for example, and then the doctor can tell the doctor's intention to the medical information providing apparatus. Accordingly, the number of program viewers can be increased because troublesome tasks are minimized.

Furthermore, the embodiment configuration can include a basic questionnaire information storing module which can be configured to store basic questionnaire information that grasps doctor's general orientation circumstances about doctor's prescription; a basic questionnaire information providing module which provides basic questionnaire information in the basic questionnaire information storing module to the doctor side terminal; a program providing order information storing module which stores multiple items of program providing order information that decide a providing order of multiple programs of the medical information program; and a program providing order selecting module which selects a program providing order based at least on an answer for the basic questionnaire information provided to the doctor side terminal and the program providing order information.

Therefore, a providing order of multiple programs can be made to an efficient order suited for the doctor's orientation of the relevant destination.

Accordingly, for example, occurrences in which a doctor who views a program stops viewing the program in the midway of the program can be decreased, and thus a program to be provided after that program will more likely be viewed, and the effect to provide a program to a destination doctor of the program can be improved.

Moreover, the configuration has the final questionnaire information storing module which stores final questionnaire information for grasping change in orientation about doctor's prescription after viewing the program; and the final questionnaire information providing module which provides final questionnaire information in the final questionnaire information storing module to the doctor side terminal.

Accordingly, the medical information providing apparatus can acquire information about change in orientation after the doctor has viewed the program on the doctor side terminal.

Besides, the configuration has the contact request questionnaire information storing module which stores multiple questionnaires on the medical information representative making contact with the doctor, as a contact request questionnaire; the contact request questionnaire information specifying module which specifies a description of a questionnaire on the medical information representative making contact with the doctor based at least on an answer for the basic questionnaire information in the individual doctor information storing module and an answer for the final questionnaire information; and the contact request questionnaire information providing module which provides to the doctor side terminal a type of contact request questionnaire information specified by the contact request questionnaire information specifying module.

More specifically, it is configured that multiple types of contacts with the medical information representative requested from the doctor are prepared in accordance with doctor's circumstances and displayed as a questionnaire on the doctor side terminal. For example, the questionnaires say 'Would you like a medical information representative to visit you?', 'Would you like to hold a briefing session at medical department?', and 'Would you like to have materials sent?.'

Whether all or a part of the questionnaires is displayed on the doctor terminal is specified based on the answers for the basic questionnaire and final questionnaire. For example, when a doctor prescribes a particular medicine a lot and a medical information representative should positively make contact with the doctor, only a questionnaire saying 'Would you like a medical information representative to visit you?' is displayed, but a questionnaire saying 'Would you like to have materials sent?' is not displayed.

In this case, an effect to encourage a medical information representative to visit the doctor is generated.

In this manner, multiple types of contact request questionnaires are prepared, the descriptions of the contact request questionnaire provided to the doctor terminal are changed based on the basic questionnaire and the final questionnaire, and thus circumstances in which a doctor desires to meet (make contact with) a medical information representative are positively produced.

Furthermore, an embodiment of the invention can include a basic questionnaire answer information input module which enters an answer for the basic questionnaire information from the doctor side terminal to the individual doctor information storing module; a final questionnaire answer information input module which enters an answer for the final questionnaire information from the doctor side terminal to the individual doctor information storing module; the contact request questionnaire answer input module which enters an answer for the contact request questionnaire from the doctor side terminal to the individual doctor information storing module; and a reference individual doctor information creating and input module which creates information in the individual doctor information storing module as reference individual doctor information for a pharmaceutical company and the medical information representative, and enters it to a reference individual doctor information storing module.

Therefore, basic questionnaire answer information, final questionnaire answer information, and contact request questionnaire answer information are all collectively stored in the individual doctor information storing module for each doctor.

Moreover, the individual doctor information storing module in which various items of information are collectively stored is the reference individual doctor information storing module as reference individual doctor information which pharmaceutical companies and medical information representatives can browse.

Accordingly, the pharmaceutical companies and the medical information representatives make access from their terminals to the medical information providing apparatus and browse the reference individual doctor information storing module, allowing them to grasp information in the medical market at doctor's personal level. More specifically, they can obtain detailed market information, and thus the pharmaceutical companies can be facilitated to configure sales strategies.

Besides, the medical information representative browses reference individual doctor information about a doctor in his/her charge, and thus can easily, promptly knows whether the doctor in his/her charge desires to make contact, and can conduct efficient activities.

According to a second aspect of the invention, in the configuration of the first aspect, the medical information providing apparatus includes: an overlap registration determination notifying module which determines whether the same information as doctor information inputted from the representative side terminal exists as the individual doctor information, and notifies the representative side terminal that it has been already registered when it exists.

According to the configuration, the fact that registration has been made beforehand can be notified to the representative, and the representative can know error promptly.

According to a third aspect of the invention, in the configuration of the first or second aspect, the medical information providing apparatus includes: a communication address information propriety determination input module which determines whether the address information is appropriate based on a communication result communicated in accordance with communication address information in the doctor side terminal, and enters its propriety in the individual doctor information storing module; and a communication address incorrect information notifying module which notifies the representative side terminal which has provided the relevant doctor specific information about the communication address information registered as incorrect on the individual doctor information storing module.

According to the configuration, error of registered communication address information can be notified to the representative side terminal promptly.

According to a fourth aspect of the invention, in the configuration of any one of the first to third aspects, the medical information providing apparatus includes: a representative presence or absence determining module which determines whether there is the representative information in the individual doctor information storing module specified by the doctor specifying module; a doctor or facility-representative information storing module which stores association information between the doctor or a facility and the representative; and a representative specifying module which specifies the representative information based on information in the individual doctor information storing module and association information between the doctor or the facility and the representative in the doctor or facility-representative information storing module.

According to the configuration, when the doctor side terminal sends access information containing identification information, a representative can be specified promptly even though no representative is registered in the corresponding individual doctor information storing module.

According to a fifth aspect of the invention, in the configuration of any one of the first to fourth aspects, the medical information providing apparatus includes: a viewing rejected program input module which stores no-viewed program information that is not viewed by the doctor side terminal in the program provided by the program providing module in the individual doctor information storing module.

According to the configuration, the pharmaceutical company refers to no-viewed program information registered in the individual doctor information storing module, and thus the contents of the no-viewed program can be removed from a brochure, allowing materials to make brochures to which the doctor pays more attention. Furthermore, since the medical information representative knows topics to which the doctor does not pay attention in conversations with the doctor, the information can be made as reference materials in usual meetings.

According to a sixth aspect of the invention, in the configuration of any one of the first to fifth aspects, the medical information providing apparatus includes: a disclosure propriety verification information sending module which sends to the doctor side terminal verification information about propriety of disclosure of the no-viewed program information, the basic questionnaire information, and an answer for the final questionnaire information, for the pharmaceutical company and medical information representative; and a disclosure propriety verification information input module which enters verification information about propriety of the disclosure from the doctor side terminal to the individual doctor information storing module, wherein as for the individual doctor information storing module on which propriety of the disclosure is registered as negative, the reference individual doctor information creating and input module changes the no-viewed program information, the answers for the basic questionnaire information and the final questionnaire information to non-disclosure status, and creates the reference individual doctor information storing module.

According to the configuration, since the pharmaceutical company and the medical information representative cannot refer to items that the doctor on the doctor side terminal does not disclose, doctor's privacy is protected.

According to a seventh aspect of the invention, in the configuration of any one of the first to sixth aspects, the medical information providing apparatus includes: a medical information representative daily report creating module which adds doctor visit information about the medical information representative in charge of the relevant doctor to the reference individual doctor information storing module, and forms it into medical information representative daily report information.

According to the configuration, since the medical information representative can use medical information representative daily report information as a daily report about visiting the doctor to be sent to his/her company, the daily report can be created easily, quickly.

More specifically, by sending medical information representative daily report information to the company, the medical information representative sends the reference individual doctor information storing module to the company into which doctor visit information has been inputted. Thus, the descriptions of the daily report are improved.

Moreover, since the pharmaceutical company having received the daily report like this can also obtain detailed information about the doctor as well as the daily report on visits, it can grasp circumstances accurately.

According to an eighth aspect of the invention, the problem can be achieved by a control method of a medical information providing apparatus which is arranged to be able to communicate with a doctor side terminal manipulated by a doctor and a representative side terminal manipulated by a medical information representative who provides medical information to the doctor, the control method including: an individual doctor information storing step wherein the medical information providing apparatus stores in an individual doctor information storing module for each doctor specific information including communication address information about the doctor side terminal specific to a doctor, doctor specialization information, and representative information, the information being inputted from the representative side terminal; an access information creating and input step wherein the medical information providing apparatus adds identification information varied for each doctor to information that permits the doctor side terminal to make access to the medical information providing apparatus, creates access information containing identification information, and enters the created access information containing identification information to the individual doctor information storing module; a medical information program selecting step wherein the medical information providing apparatus selects a medical information program, based on the doctor specialization information, from a medical information program storing module which classifies the medical information program formed of multiple programs to be provided to the doctor side terminal into each item of the doctor specialization information for storage; a program guide information creating and sending step wherein the medical information providing apparatus creates and sends program providing guide information for acquiring consent to send the selected medical information program based on the communication address information in the individual doctor information storing module and the access information containing identification information; a doctor specifying step wherein the medical information providing apparatus specifies the relevant individual doctor information storing module from the sent identification information when the access information containing identification information added to the program guide information is sent from the doctor side terminal to the medical information providing apparatus; a basic questionnaire information providing step wherein the medical information providing apparatus provides to the doctor side terminal basic questionnaire information in a basic questionnaire information storing module which stores basic questionnaire information for grasping doctor's general orientation circumstances about doctor's prescription; a program providing order selecting step wherein the medical information providing apparatus selects a program providing order based at least on an answer for the basic questionnaire information provided to the doctor side terminal and on multiple items of program providing order information that are stored in a program providing order information storing module and decide a providing order of multiple programs of the medical information program; a program providing step wherein the medical information providing apparatus provides a program to the doctor side terminal based on program providing order information selected at the program providing order selecting step; a basic questionnaire answer information input step wherein the medical information providing apparatus enters an answer for the basic questionnaire information from the doctor side terminal to the individual doctor information storing module; a final questionnaire information providing step wherein the medical information providing apparatus provides to the doctor side terminal final questionnaire information that is stored in a final questionnaire information storing module for grasping change in orientation about doctor's prescription after viewing the program; a final questionnaire answer information input step wherein the medical information providing apparatus enters an answer for the final questionnaire information from the doctor side terminal to the individual doctor information storing module; a contact request questionnaire information specifying step wherein the medical information providing apparatus specifies a description of a questionnaire for the doctor based at least on an answer for the basic questionnaire information in the individual doctor information storing module and an answer for the final questionnaire information; a contact request questionnaire information providing step wherein the medical information providing apparatus provides to the doctor side terminal a type of contact request questionnaire information specified by the contact request questionnaire information specifying module; a contact request questionnaire answer input step wherein the medical information providing apparatus enters an answer for the contact request questionnaire from the doctor side terminal to the individual doctor information storing module; and a reference individual doctor information creating and input step wherein the medical information providing apparatus creates information in the individual doctor information storing module as reference individual doctor information for a pharmaceutical company and the medical information representative, and enters it to a reference individual doctor information storing module.

According to a ninth aspect of the invention, the problem can be achieved by a control program of a medical information providing apparatus which is arranged to be able to communicate with a doctor side terminal manipulated by a doctor and a representative side terminal manipulated by a medical information representative who provides medical information to the doctor, the control program allowing a computer to implement: an individual doctor information storing step wherein the medical information providing apparatus stores in an individual doctor information storing module for each doctor specific information including communication address information about the doctor side terminal specific to a doctor, doctor specialization information, and representative information, the information being inputted from the representative side terminal; an access information creating and input step wherein the medical information providing apparatus adds identification information varied for each doctor to information that permits the doctor side terminal to make access to the medical information providing apparatus, creates access information containing identification information, and enters the created access information containing identification information to the individual doctor information storing module; a medical information program selecting step wherein the medical information providing apparatus selects a medical information program, based on the doctor specialization information, from a medical information program storing module which classifies the medical information program formed of multiple programs to be provided to the doctor side terminal into each item of the doctor specialization information for storage; a program guide information creating and sending step wherein the medical information providing apparatus creates and sends program providing guide information for acquiring consent to send the selected medical information program based on the communication address information in the individual doctor information storing module and the access information containing identification information; a doctor specifying step wherein the medical information providing apparatus specifies the relevant individual doctor information storing module from the sent identification information when the access information containing identification information added to the program guide information is sent from the doctor side terminal to the medical information providing apparatus; a basic questionnaire information providing step wherein the medical information providing apparatus provides to the doctor side terminal basic questionnaire information in a basic questionnaire information storing module which stores basic questionnaire information for grasping doctor's general orientation circumstances about doctor's prescription; a program providing order selecting step wherein the medical information providing apparatus selects a program providing order based at least on an answer for the basic questionnaire information provided to the doctor side terminal and on multiple items of program providing order information that are stored in a program providing order information storing module and decide a providing order of multiple programs of the medical information program; a program providing step wherein the medical information providing apparatus provides a program to the doctor side terminal based on program providing order information selected at the program providing order selecting step; a basic questionnaire answer information input step wherein the medical information providing apparatus enters an answer for the basic questionnaire information from the doctor side terminal to the individual doctor information storing module; a final questionnaire information providing step wherein the medical information providing apparatus provides to the doctor side terminal final questionnaire information that is stored in a final questionnaire information storing module for grasping change in orientation about doctor's prescription after viewing the program; a final questionnaire answer information input step wherein the medical information providing apparatus enters an answer for the final questionnaire information from the doctor side terminal to the individual doctor information storing module; a contact request questionnaire information specifying step wherein the medical information providing apparatus specifies a description of a questionnaire for the doctor based at least on an answer for the basic questionnaire information in the individual doctor information storing module and an answer for the final questionnaire information; a contact request questionnaire information providing step wherein the medical information providing apparatus provides to the doctor side terminal a type of contact request questionnaire information specified by the contact request questionnaire information specifying module; a contact request questionnaire answer input step wherein the medical information providing apparatus enters an answer for the contact request questionnaire from the doctor side terminal to the individual doctor information storing module; and a reference individual doctor information creating and input step wherein the medical information providing apparatus creates information in the individual doctor information storing module as reference individual doctor information for a pharmaceutical company and the medical information representative, and enters it to a reference individual doctor information storing module.

According to a tenth aspect of the invention, the problem can be achieved by a computer readable recording medium recorded with a control program of a medical information providing apparatus which is arranged to be able to communicate with a doctor side terminal manipulated by a doctor and a representative side terminal manipulated by a medical information representative who provides medical information to the doctor, the control program allowing a computer to implement: an individual doctor information storing step wherein the medical information providing apparatus stores in an individual doctor information storing module for each doctor specific information including communication address information about the doctor side terminal specific to a doctor, doctor specialization information, and representative information, the information being inputted from the representative side terminal; an access information creating and input step wherein the medical information providing apparatus adds identification information varied for each doctor to information that permits the doctor side terminal to make access to the medical information providing apparatus, creates access information containing identification information, and enters the created access information containing identification information to the individual doctor information storing module; a medical information program selecting step wherein the medical information providing apparatus selects a medical information program, based on the doctor specialization information, from a medical information program storing module which classifies the medical information program formed of multiple programs to be provided to the doctor side terminal into each item of the doctor specialization information for storage; a program guide information creating and sending step wherein the medical information providing apparatus creates and sends program providing guide information for acquiring consent to send the selected medical information program based on the communication address information in the individual doctor information storing module and the access information containing identification information; a doctor specifying step wherein the medical information providing apparatus specifies the relevant individual doctor information storing module from the sent identification information when the access information containing identification information added to the program guide information is sent from the doctor side terminal to the medical information providing apparatus; a basic questionnaire information providing step wherein the medical information providing apparatus provides to the doctor side terminal basic questionnaire information in a basic questionnaire information storing module which stores basic questionnaire information for grasping doctor's general orientation circumstances about doctor's prescription; a program providing order selecting step wherein the medical information providing apparatus selects a program providing order based at least on an answer for the basic questionnaire information provided to the doctor side terminal and on multiple items of program providing order information that are stored in a program providing order information storing module and decide a providing order of multiple programs of the medical information program; a program providing step wherein the medical information providing apparatus provides a program to the doctor side terminal based on program providing order information selected at the program providing order selecting step; a basic questionnaire answer information input step wherein the medical information providing apparatus enters an answer for the basic questionnaire information from the doctor side terminal to the individual doctor information storing module; a final questionnaire information providing step wherein the medical information providing apparatus provides to the doctor side terminal final questionnaire information that is stored in a final questionnaire information storing module for grasping change in orientation about doctor's prescription after viewing the program; a final questionnaire answer information input step wherein the medical information providing apparatus enters an answer for the final questionnaire information from the doctor side terminal to the individual doctor information storing module; a contact request questionnaire information specifying step wherein the medical information providing apparatus specifies a description of a questionnaire for the doctor based at least on an answer for the basic questionnaire information in the individual doctor information storing module and an answer for the final questionnaire information; a contact request questionnaire information providing step wherein the medical information providing apparatus provides to the doctor side terminal a type of contact request questionnaire information specified by the contact request questionnaire information specifying module; a contact request questionnaire answer input step wherein the medical information providing apparatus enters an answer for the contact request questionnaire from the doctor side terminal to the individual doctor information storing module; and a reference individual doctor information creating and input step wherein the medical information providing apparatus creates information in the individual doctor information storing module as reference individual doctor information for a pharmaceutical company and the medical information representative, and enters it to a reference individual doctor information storing module.

The medical information providing apparatus, the control method of the medical information providing apparatus, the control program of the medical information providing apparatus, and the computer readable recording medium recorded with control program of the medical information providing apparatus according to the invention have advantages that can increase the number of doctor side terminals to be destinations of program distribution with no cost increase, can acquire market information extended in detail to doctor's personal level from the answer for the doctor's questionnaire and provide it to the pharmaceutical company and the MR, can positively produce circumstances in which the doctor desires to make contact with the MR, and can transmit to the MR and the pharmaceutical company promptly information about the doctor who desires to make such contact.

BRIEF DESCRIPTION OF THE DRAWINGS

The embodiments of the invention can be readily understood by considering the following detailed description in conjunction with the accompanying drawings, in which:

FIG. 1 is a schematic block diagram illustrating a medical information providing system using a medical information providing apparatus according to the invention;

FIG. 2 is a schematic diagram illustrating the main hardware configuration of a doctor terminal, an MR terminal, a pharmaceutical company management department terminal, and a medical information providing server shown in FIG. 1;

FIG. 4 is exemplary data depicting an example of a doctor specific file;

FIG. 5 is exemplary data showing descriptions of the program information file shown in FIG. 3;

FIG. 6 is an exemplary hospital and representative list table;

FIG. 7 is an exemplary probing questionnaire file;

FIG. 8 is an exemplary program providing order file;

FIG. 9 is an exemplary closing questionnaire file;

FIG. 10 is an exemplary MR contact request questionnaire file;

FIG. 11 is an exemplary reference doctor specific file;

FIG. 12 is an exemplary MR daily report;

FIG. 15 is another flow chart schematically illustrating the steps that medical information providing server provides a program to a doctor terminal; and FIG. 16 is a flow chart schematically illustrating the steps that the medical information providing server provides a program to doctor terminal.

DESCRIPTION OF PREFERRED EMBODIMENTS

Figure 3:
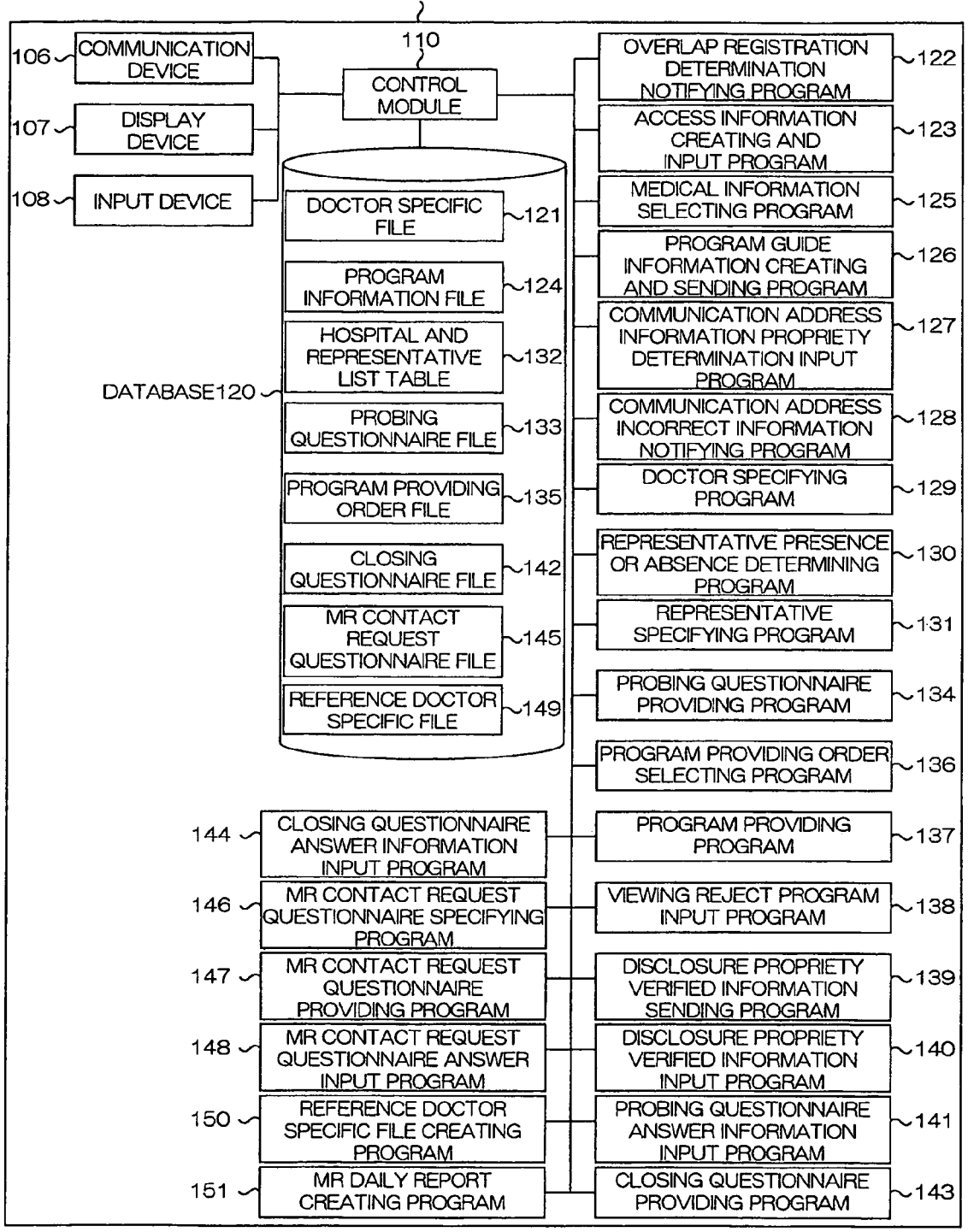
FIG. 3 is a schematic diagram illustrating the main software configuration of the medical information providing server.

Hereinafter, exemplary embodiments of the invention will be described in detail with reference to the accompanying drawings.

In addition, the embodiments described below are specific examples of the invention. Therefore, various technically optimal or beneficial features are incorporated, but the scope of the invention is not limited to the embodiments.

FIG. 1 is a schematic block diagram illustrating a medical information providing system 10 using a medical information providing apparatus according to the invention.

As shown in FIG. 1, the medical information providing system 10 has a doctor terminal 11, for example, that is a doctor side terminal which is placed at a hospital and manipulated by a doctor, and an MR terminal 12, for example, that is a representative side terminal which is placed at a pharmaceutical company and manipulated by a medical information representative (MR) who provides medical information for a doctor.

In addition, at the pharmaceutical company, a pharmaceutical company management department terminal 13 is also placed, which is manipulated by a pharmaceutical company management department that manages the MR.

Moreover, at a company that provides medical information providing services, a medical information providing server 100 is placed, for example, that is a medical information providing apparatus.

Then, the doctor terminal 11, the MR terminal 12, and the pharmaceutical company management department terminal 13 are connected to the medical information providing server 100 through an Internet network 14, for example, in such a way that they can communicate with each other.

FIG. 2 is a schematic diagram illustrating the main hardware configuration of the doctor terminal 11, the MR terminal 12, the pharmaceutical company management department terminal 13, and the medical information providing server 100 shown in FIG. 1.

Since they are all configured of computers, the configuration of the doctor terminal 11 will be described, omitting the description for the others.

As shown in FIG. 2, the computer of the doctor terminal 11 has a bus 101. The bus 101 is arranged with a CPU (Central Processing Unit) 102, RAM (Random Access Memory) 103, ROM (Read Only Memory) 104, and a hard disk drive 105.

Furthermore, the bus 101 is connected to a communication device 106 which can communicate with the Internet network 14, a display device 107, and an input device 108 such as a keyboard.

In the meantime, the bus 101 has a function that connects all the devices, and is an internal path having addresses and data paths.

The CPU 102 processes predetermined programs as well as controls devices such as the ROM 104 connected to the bus 101. The ROM 104 stores various programs and various items of information therein.

The RAM 103 has a function as an area that compares data in memory in processing a program and runs programs.

Besides, since the computer is connected to the Internet network 14, it is configured to display a browser that can read a file written in the HTML language on a display 107. For the browser, various browser software programs of HTML browsing software, for example, are applied.

Furthermore, for example, it is configured that basic control programs (OS (operating system) and BIOS (basic output control system)) installed in the computer are operated by TCP/IP (Transmission Control Protocol/Internet Protocol) and Java (trademark) language.

FIG. 3 is a schematic diagram illustrating the main software configuration of the medical information providing server 100. As shown in FIG. 3, the medical information providing server 100 has a control module 110. The control module 110 controls the input device 108, the display 107, and the communication device 106 shown in FIG. 2 as well as runs various programs shown in FIG. 3. Then, it also manages data in a database 120.

Hereinafter, it will be described more specifically.

First, the medical information providing server 100 has a doctor specific file storing module 121, for example, that is an individual doctor information storing module.

The doctor specific file 121 stores doctor specific information for each doctor, including address information that is a mail address for communications of the doctor terminal 11 specific to a doctor and inputted from the MR terminal 12, and specialization information that is doctor a clinical department, and a name of an MR in charge that is representative information.

FIG. 4 is exemplary data depicting an example of the doctor specific file 121. As shown in FIG. 4, the doctor specific file 121 is created for each doctor. In FIG. 3, although only a single doctor specific file 121 is shown and the others are omitted, the doctor specific file 121 is arranged in accordance with the number of registered doctors in practice.

Moreover, the medical information providing server 100 is formed with an overlap registration determination notifying module, for example, an overlap registration determination notifying program 122 which determines whether there is the same information as doctor information inputted from the MR terminal 12 as the doctor specific file 121, and notifies the MR terminal 12 that it has been already registered when it exists.

Besides, the medical information providing server 100 has an access information creating and input module, for example, an access information creating and input program 123 which creates information for making access to the medical information providing server 100 by the doctor terminal 11 in such a way that it adds an identification symbol to a URL to create a URL with identification information different for each doctor and registers the created URL with an identification symbol on the doctor specific file 121 (see FIG. 4).

Furthermore, the medical information providing server 100 has a medical information program storing module, for example, a program information file 124 which classifies medical information programs formed of multiple programs provided to the doctor terminal 11 into each clinical department.

In FIG. 3, although only a single program information file 124 is shown, a number of the program information files 124 are formed each of which has the descriptions varied at each clinical department in practice.

FIG. 5 is exemplary data which shows the descriptions of the program information file 124 shown in FIG. 3. As shown in FIG. 5, programs are separated into six programs, and the clinical department is internal medicine.

Thus, medical information programs suitable for the registered doctor's specialty registered in the doctor specific file 121 can be provided to the doctor terminal 11 of the doctor, and programs fit to the orientation of the doctor can be provided efficiently.

Moreover, the medical information providing server 100 is formed with a medical information selecting module, for example, a medical information selecting program 125 which selects the program information file 124 based on clinical department information in the doctor specific file 121 shown in FIG. 4.

In the example shown in FIG. 4, clinical department is internal medicine and the clinical department of the program information file 124 shown in FIG. 5 is internal medicine. Therefore, as a program for Dr. KONO Taro in FIG. 4, 'sleeping pills' in FIG. 5 is to be selected.

Besides, the medical information providing server 100 has a program guide information creating and sending module, for example, a program guide information creating and sending program 126. The program guide information creating and sending program 126 creates program providing guide information, for example, an e-mail which obtains consent whether the selected program 'sleeping pills' in FIG. 5 is sent to Dr. KONO Taro's doctor side terminal 11 in FIG. 4. This e-mail is configured in which it is attached with the URL with an identification symbol of the doctor specific file 121 shown in FIG. 4, and the e-mail attached with the URL is sent to the mail address in FIG. 4.

Furthermore, the medical information providing server 100 is formed with a communication address information propriety determination input module, for example, a communication address information propriety determination input program 127 which communicates in accordance with a mail address in FIG. 4, consequently determines whether this mail address is appropriate, and enters 'NO' for propriety in the mail address in the doctor specific file 121 in FIG. 4 when it receives a non-affirmation message.

Moreover, the medical information providing server 100 is formed with a communication address incorrect information notifying module, for example, a communication address incorrect information notifying program 128 which notifies the MR terminal 12 of an MR in charge (in FIG. 4, HEIYAMA Saburo) who enter doctor (KONO Taro) information about the mail address registered as the propriety of the mail address is non-affirmative in the doctor specific file 121 in FIG. 4.

Besides, the medical information providing server 100 has a doctor specifying module, for example, a doctor specifying program 129. More specifically, when the doctor who has received the e-mail attached with the URL with an identification symbol sent by the program guide information creating and sending program 126 in FIG. 3 clicks the relevant URL by the doctor terminal 11, this information is sent to the medical information providing server 100.

When it receives this information, the doctor specifying program 129 selects the relevant doctor specific file 121 from the sent identification symbol.

In the embodiment, the doctor specific file 121 of Dr. KONO Taro in FIG. 4, for example, is selected.

Furthermore, the medical information providing server 100 has a representative presence or absence determining module, for example, a representative presence or absence determining program 130 which determines whether an MR's name in charge is borne on a column of MR in charge in the doctor specific file 121 specified by the doctor specifying program 129 (see FIG. 4).

In the example shown in FIG. 4, the MR in charge is borne, but suppose when it is not borne, a representative specifying program 131, for example, a representative specifying module operates.

More specifically, the medical information providing server 100 has a doctor or facility-representative information storing module, for example, a hospital and representative list table 132 which stores association information between a doctor or facility and a representative.

FIG. 6 is an example of the hospital and representative list table 132. As shown in FIG. 6, a hospital name, a clinical department, and an MR in charge are registered as table information.

Moreover, the representative specifying program 131 refers to the hospital and representative list table 132 and specifies the MR in charge for the relevant doctor.

Besides, the medical information providing server 100 has a basic questionnaire information storing module, which stores basic questionnaire information for having knowledge of doctor's general orientation circumstances about doctor's prescription, for example, a probing questionnaire. A probing questionnaire file 133 shown in FIG. 3 is an example of the basic questionnaire information storing module.

FIG. 7 is an example of the probing questionnaire file 133. As shown in FIG. 7, the probing questionnaire is formed of the number of patients, recognition medicines, medicine use circumstances, and the number of patients of specific diseases.

More specifically, it is configured that the probing questionnaire is performed to grasp the current doctor's circumstances.

Furthermore, the medical information providing server 100 has a basic questionnaire providing module, for example, a probing questionnaire providing program 134 which provides such probing questionnaires for target doctors, for example, to the doctor terminal 11 of Dr. KONO Taro in FIG. 4.

Moreover, the medical information providing server 100 has a program providing order information storing module, for example, a program providing order file 135 which stores multiple items of program providing order information that decide the order of providing multiple programs in the program providing file 124 in FIG. 5, for example, each of contents 1 to 6 in FIG. 5.

FIG. 8 is an example of the program providing order file 135. As shown in FIG. 8, providing orders of programs in eight patterns, for example, are registered.

Besides, the medical information providing server 100 has a program providing order selecting module, for example, a program providing order selecting program 136 which selects a pattern for a program providing order based on the doctor's answer for the probing questionnaire and data in the program providing order file 135 in FIG. 8.

For example, when it is the doctor who has been distributed the same program before and the probing questionnaire result saying that the number of hypertension patients is ten or greater per month and the doctor has prescribed sleeping pill A in FIG. 7, the program providing order is set from 6 to 3 to 4 to 5 to 2 to 1, as shown in FIG. 8.

More specifically, it is configured that instead of contents 1 to 3 that are general, contents 6 that are useful for practical prescription are first provided for the doctor who has already prescribed many times. Thus, contents are fit to the doctor's orientation, and the doctor is prevented from stopping viewing programs during distribution.

Furthermore, the medical information providing server 100 has a program providing module, for example, a program providing program 137 which provides programs to the doctor terminal 11 based on the program providing order selected by the program providing order selecting program 136.

Moreover, the medical information providing server 100 has a viewing rejected program input module, for example, a viewing rejected program input program 138 which registers on the viewing rejected program in FIG. 4 no-viewed program information about a program that has not been viewed by the doctor terminal 11 among the programs provided by the program providing program 137, 'sleeping pills', for example, in FIG. 5 (for example, contents 2 was not viewed in FIG. 5).

Besides, the medical information providing server 100 has a disclosure propriety verification information sending module, for example, a disclosure propriety verification information sending program 139 which sends to the doctor terminal 11 verification information whether it is appropriate to disclose viewing rejected program information, answer information about the probing questionnaire, and answer information about a closing questionnaire, described later, in FIG. 4 to a pharmaceutical company and an MR.

Furthermore, the medical information providing server 100 has a disclosure propriety verification information input module, for example, a disclosure propriety verification information input program 140 which enters 'verification information about propriety of disclosure' received from the doctor terminal 11 to a column of 'disclosure of the program viewing result to a pharmaceutical company' in the doctor specific file 121 in FIG. 4.

Moreover, the medical information providing server 100 has a basic questionnaire answer information input module, for example, a probing questionnaire answer information input program 141 which enters the answer for the probing questionnaire sent from the doctor terminal 11 to a 'probing questionnaire result' in the doctor specific file 121 in FIG. 4.

Besides, the medical information providing server 100 has a final questionnaire information storing module, for example, a closing questionnaire file 142 which stores the closing questionnaire that is a final questionnaire for grasping change in orientation on doctor's prescription after viewing the programs about sleeping pills.

FIG. 9 is an example of the closing questionnaire file 142. As shown in FIG. 9, it is a questionnaire whether the tendency to prescribe medicines is changed after the doctor viewed the programs.

Furthermore, the medical information providing server 100 has a closing questionnaire providing program 143 which provides the closing questionnaire in the closing questionnaire file 142 to the doctor terminal 11.

Moreover, it has a final questionnaire answer information input module, for example, a closing questionnaire answer information input program 144 which enters the answer for the closing questionnaire from the doctor terminal 11 having received the closing questionnaire to a 'closing questionnaire result' in the doctor specific file 121 in FIG. 4.

Besides, it has a contact request questionnaire information storing module which stores multiple questionnaires about an MR making contact with a doctor as an MR contact request questionnaire. This contact request questionnaire information storing module is an MR contact request questionnaire file 145, for example.

FIG. 10 is an example of the MR contact request questionnaire file 145. As shown in FIG. 10, the MR contact request questionnaire file 145 is registered with three types of contact questionnaires saying, 'Would you like an MR to visit you?', 'Would you like to have materials sent?', and 'Would you like to hold a briefing session at medical department?'.

Furthermore, it is registered with the combinations and conditions of presenting these types of questionnaires to the doctor terminal 11.

For example, it is configured that for a doctor in great demand who cares 30 or more patients and ten or more specific disease patients in the probing questionnaire and positively adopts three boxes or greater in the closing questionnaire, only the questionnaire saying, 'Would you like an MR to visit you?' is presented, and thus an MR is guided to visit that doctor easily.

Moreover, it has a contact request questionnaire information specifying module, for example, an MR contact request questionnaire specifying program 146 which specifies an MR contact pattern in FIG. 10 based on the probing questionnaire result and the closing questionnaire result in the doctor specific file 121 in FIG. 4.

Besides, the medical information providing server 100 has a contact request questionnaire information providing module, for example, an MR contact request questionnaire providing program 147 which provides the questionnaire in the pattern in FIG. 10 specified by the MR contact request questionnaire specifying program 146 to the doctor terminal 11.

Furthermore, it is formed with a contact request questionnaire answer input module, for example, an MR contact request questionnaire answer input program 148 which enters the answer for the MR contact request questionnaire from the doctor terminal 11 to a column of 'MR contact request' in the doctor specific file 121 in FIG. 4.

Moreover, the medical information providing server 100 has a reference individual doctor information creating and input module, for example, a reference doctor specific file creating program 150 which creates information in the doctor specific file 121 in FIG. 4 as reference individual doctor information for a pharmaceutical company and an MR, and enters it to a reference individual doctor information storing module, for example, a reference doctor specific file 149.

In the reference doctor specific file creating program 150, when it is registered that disclosure is inappropriate in the doctor specific file 121 in FIG. 4, these items are changed to non-disclosure status for registration in the reference doctor specific file 149.

FIG. 11 is an example of the reference doctor specific file 149. In this file, it is in the status that items for non-disclosure selected by the doctor are not disclosed.

Besides, it is also formed with an MR daily report creating module, for example, an MR daily report creating program 151 which adds doctor visit information about the MR in charge of that doctor to the reference doctor specific file 149 for MR daily report information.

FIG. 12 is an exemplary MR daily report. As shown in FIG. 12, 'MR contact information' is added in the reference doctor specific file 149 in FIG. 11.

The medical information providing system 10 according to the embodiment is configured as described above. Hereinafter, the operation thereof will be described in detail.

Figure 13:
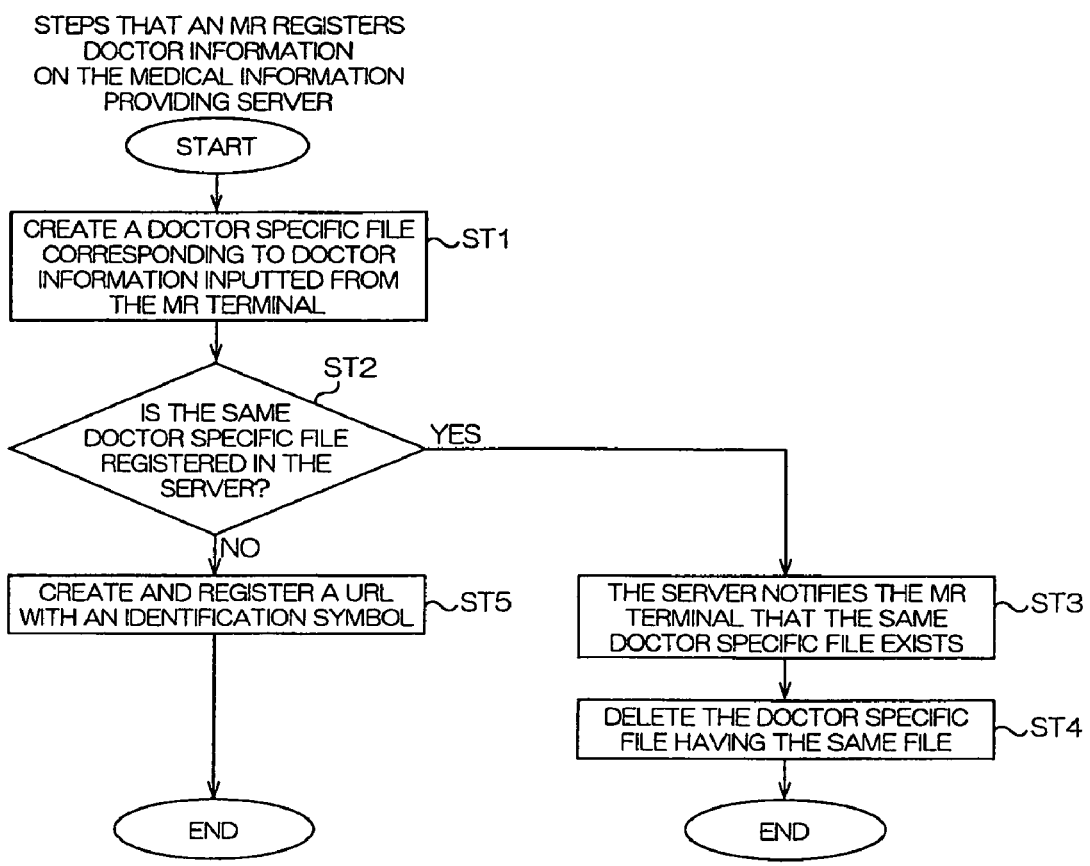
FIG. 13 is a flow chart schematically illustrating the steps that an MR registers doctor information on the medical information providing server.

FIG. 13 is a flow chart schematically illustrating the steps that an MR registers doctor information on the medical information providing server 100.

First, at ST1, the MR terminal creates the doctor specific file 121 (FIG. 4) corresponding to doctor information (an exemplary individual doctor information storing step).

Therefore, the medical information providing server 100 is configured to positively accept doctor specific information from the MR, when the MR positively offers doctor specific information about doctors whom the MR knows.

Thus, an administrator of the medical information providing server 100 can increase the number of new doctor terminals 11 registered by the MR terminal 12 without looking for new doctor terminals 11 to be destinations of medical information programs at cost.

Furthermore, an increased number of doctor terminals 11 registered allow the medical information providing server 100 to provide medical information program to a larger number of doctor terminals 11.

Accordingly, the medical information providing server 100 can increase the destinations to distribute medical information programs with no cost increase.

Then, at ST2, the overlap registration determination notifying program 122 in FIG. 3 determines whether the same doctor specific file is registered in the medical information providing server 100. When it is registered, as shown in ST3, the MR terminal 12 is notified that the same doctor specific file exists.

Therefore, the fact that registration has already done can be notified to the MR who has offered doctor information, and thus the MR can know error promptly.

Subsequently, the doctor specific file having the same file is deleted from the medical information providing server 100 (ST4).

On the other hand, when the same file does not exist, the access information creating and input program 123 in FIG. 3 creates access information containing identification symbol corresponding to the doctor specific file 121 created at ST1, and registers it on a 'URL with an identification symbol' in the doctor specific file 121 (ST5) (an exemplary access information creating and input step).

As described above, the steps that the MR registers doctor information on the medical information providing server 100 are ended.

Figure 14:
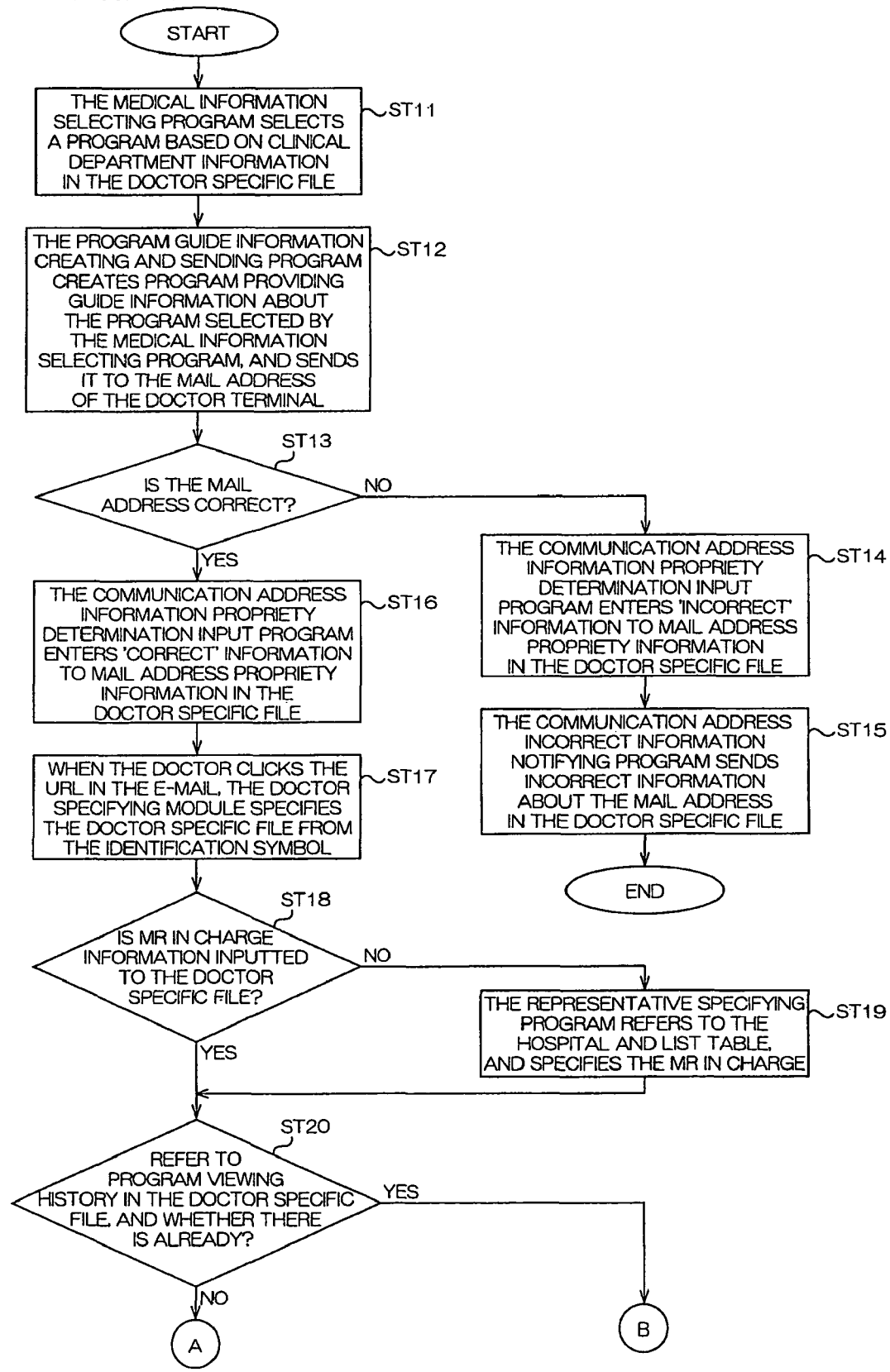
FIG. 14 is a flow chart schematically illustrating the steps that the medical information providing server provides a program to a doctor terminal.

FIGS. 14 to 16 are flow charts schematically illustrating the steps that the medical information providing server 100 provides a program to the doctor terminal 11.

First, as shown in ST11, the medical information selecting program 125 selects a program (for example, the program 'sleeping pills' in FIG. 5) based on clinical department information in the doctor specific file (for example, a column of 'clinical department' in the doctor specific file 121 in FIG. 4) (an exemplary medical information program selecting step).

Therefore, a program suited for the registered doctor's specialty can be provided, and the program fit to the doctor's orientation can be provided efficiently.

Subsequently, as shown in ST12, the program guide information creating and sending program 126 creates program providing guide information (an e-mail added with a URL with an identification symbol) about the program ('sleeping pills' selected by the medical information selecting program 125, the e-mail being the created program providing guide information is sent to the mail address of the doctor terminal 11 (for example, the terminal of Dr. KONO Taro in FIG. 4) (program guide information creating and sending step).

Then, at ST13, the mail address sent is determined whether it is correct. More specifically, when the communication address information propriety determination input program 127 receives a non-affirmation message about the mail address, it determines that the mail address is incorrect, whereas it determines that it is correct when otherwise.

When the mail address is determined as incorrect, the communication address information propriety determination input program 127 enters 'INCORRECT' in a column of 'mail address propriety' in the doctor specific file 121 (ST14).

Subsequently, the communication address incorrect information notifying program 128 sends the fact that the mail address is incorrect to the MR terminal 12 of the MR having offered at ST1 in FIG. 13 doctor information about the doctor in the doctor specific file 121 to which 'INCORRECT' is inputted (ST15), and the steps are ended.

Therefore, the MR having offered doctor information can promptly know error about the mail address that the MR offered, and the MR can quickly respond thereafter.

On the other hand, when the mail address is determined as correct at ST13, the communication address information propriety determination input program 127 enters 'CORRECT' to the column of 'mail address propriety' in the doctor specific file 121 (ST16).

Then, when a doctor who has received the e-mail being program providing guide information clicks the 'URL' presented in the e-mail, the doctor specifying program 129 of the medical information providing server 100 specifies the doctor specific file 121 of that doctor from the identification symbol attached to the URL (ST17) (an exemplary doctor specifying step).

Thus, a doctor only clicking the URL allows the medical information providing server 100 to promptly specify the doctor who has clicked.

Therefore, a doctor who desires to view a program only clicks the URL on the screen of the doctor terminal 11 to tell the doctor's intention to the medical information providing server 100, and thus the doctor will not have any troublesome task. Accordingly, the number of doctors who view programs can be increased.

Subsequently, the representative presence or absence determining program 130 refers to the column of 'MR in charge' in the doctor specific file 121 specified at ST17, and it determines whether the MR in charge is registered (ST18).

When any MR is not registered, the representative specifying program 131 refers to the hospital and list table 132 (see FIG. 6), and specifies the MR in charge (ST19).

Thus, the MR in charge can be decided promptly. More specifically, since a doctor who desires to view a program can be expected to prescribe future medicine prescriptions, the status that the MR in charge is absence needs to be solved quickly. In this point, the embodiment can solve such the event.

Then, as shown in ST20, the medical information providing server 100 refers to a column of 'program viewing history' in the doctor specific file. When there is no program viewing history, '1. opening contents (history of sleeping pills)' in the program 'sleeping pills' in FIG. 5, for example, is provided to the relevant doctor terminal 11 (ST21).

Subsequently, before providing the program contents, the probing questionnaire providing program 134 provides a probing questionnaire in the probing questionnaire file 133 (for example, a questionnaire in FIG. 7 saying, 'How many insomnia patients do you care?') to the doctor terminal 11 (ST22) (an exemplary basic questionnaire information providing step).

Subsequently, based on the answer for the probing questionnaire sent back from the doctor and the program providing order file 135, the program providing order selecting program 136 selects a program providing order (ST23) (an exemplary program order selecting step).

More specifically, in accordance with the conditions of the program providing order file 135 in FIG. 8, a program providing order is decided. For example, in FIG. 8, when the doctor specific file 121 describes that a doctor has history of program distribution, and answers in the probing questionnaire that he cares ten or more hypertension patients per month, and has prescribed sleeping pill A, a program providing order in FIG. 5, that is, a providing order of contents starts from '6. Treatment of transient and short term insomnia' to '3' to '4' to '5' to '2' to '1', and it is a program order fit to the prescribed doctor's orientation.

In this manner, in the embodiment, the probing questionnaire is used to allow a providing order of multiple programs (contents) to meet the doctor's orientation of the destination for the programs, and an efficient program providing order can be made.

Accordingly, for example, such an event can be prevented from occurring that a doctor stops viewing in the midway of certain contents during a program and will not view contents provided after those contents, and the effect for the doctor viewing programs can be enhanced.

Subsequently, the program providing program 137 distributes the program ('sleeping pills') in the selected program providing order (for example, 'providing pattern 1' in FIG. 8) to the doctor terminal 11 (ST24) (an exemplary program providing step).

When the doctor finishes viewing the program, the viewing rejected program input program 138 then determines whether there is a program (contents) that the doctor has not viewed (ST25).

When there is a no-viewed program that is a program not viewed, that program (for example, '2. sleeping pills to be sought' in FIG. 5) is listed in a column of 'viewing rejected program' in the doctor specific file 121 in FIG. 4.

When a pharmaceutical company refers to such information about viewing rejected programs, it will be reference materials to make future brochures. More specifically, the contents of the programs that the doctor has rejected viewing are removed from brochures to make efficient brochures for the doctor.

Furthermore, since the MR can also grasp topics to which the doctor does not pay attention by knowing viewing rejected programs, the MR can make reference materials for usual meetings.

Subsequently, the disclosure propriety verification information sending program 138 sends to the doctor terminal 11 verification information about whether the viewing rejected program, and the answers for the probing questionnaire and closing questionnaire are disclosed to a pharmaceutical company and an MR (ST28).

In response to the reply from the doctor, the disclosure propriety verification information input program 140 enters 'YES' or 'NO' in a column of 'disclosure of the program viewing result to pharmaceutical companies' in the doctor specific file 121 (ST29, ST30).

Then, the probing questionnaire answer information input program 141 registers the answer for the probing questionnaire on the doctor specific file 121 (ST31) (an exemplary basic questionnaire answer information input step).

Subsequently, the medical information providing server 100 refers to the medicine use circumstance result in the probing questionnaire, and determines whether 'sleeping pill A' has been prescribed, for example, (ST32).

Then, the closing questionnaire providing program 143 selects a closing questionnaire from the closing questionnaire file in accordance with information of whether the doctor has used or not used the medicine, and provides it to the doctor terminal 11 (ST33, ST34) (an exemplary final questionnaire information providing step).

The descriptions of the closing questionnaire are the description that can be understood the change in the doctor's orientation after the program has been viewed, particularly, the change in the prescription orientation.

Subsequently, when a reply for the closing questionnaire is received from the doctor, the closing questionnaire answer information input program 144 enters the result in a column of 'closing questionnaire result' in the doctor specific file 121 (ST35) (an exemplary final questionnaire answer information input step).

Then, the MR contact request questionnaire specifying program 146 specifies the descriptions of the MR contact request questionnaire based on information in the doctor specific file 121 and information in the MR contact request questionnaire file 145 (ST36) (contact request questionnaire information specifying step).

More specifically, as shown in FIG. 10, the MR contact request questionnaire says, 'Would you like an MR to visit you?', 'Would you like to have materials sent?' and 'Would you like to hold a briefing session at medical department?'

The MR contact request questionnaire specifying program 146 specifies whether all or a part of the questionnaires is displayed on the doctor terminal 11, and information in the doctor specific file 121 and information in the MR contact request questionnaire file 145 are used in specifying it.

For example, in the case of a doctor who cares 30 or more patients and ten or more specific disease patients, and intends to adopt a medicine in three or more boxes, an increase in prescriptions is expected, and thus it is the case where an MR should positively make contact with that doctor.

In this case, only a questionnaire saying, 'Would you like an MR to visit you?' is displayed, but a questionnaire saying, 'Would you like to have materials sent?' is not displayed.

Therefore, an effect to encourage a medical information representative to visit the doctor is generated.

In this manner, it is configured that multiple types of contact request questionnaires are prepared, the descriptions of the contact request questionnaire provided to the doctor terminal 11 are changed based on the probing questionnaire and closing questionnaire, and thus circumstances that a doctor desires to meet (make contact with) an MR are positively produced.

Subsequently, the MR contact request questionnaire providing program 147 provides only a questionnaire specified by the MR contact request questionnaire specifying program 146, 'Would you like an MR to visit you?', for example, to the doctor terminal 11 (ST37) (an exemplary contact request questionnaire information providing step).

Then, when a reply for the questionnaire is received from the doctor, the MR contact request questionnaire answer input program 148 enters the answer for the MR contact request questionnaire in a column of 'MR contact request' in the doctor specific file 121 (ST38) (an exemplary contact request questionnaire answer input step).

Subsequently, the reference doctor specific file creating program 150 creates the reference doctor specific file 149 as shown in FIG. 11 (ST39) (an exemplary reference individual doctor information creating and input step).

At this time, when the column of 'disclosure of the program viewing result to pharmaceutical companies' is 'NO' in the doctor specific file 121 in FIG. 4, the relevant portion is not disclosed.

Doctor's privacy can be protected, even when the reference doctor specific file 149 thus created is disclosed to an MR and a pharmaceutical company's management department.

In addition, the reference doctor specific file 149 thus created is disclosed to an MR and a pharmaceutical company's management department.

On the reference doctor specific file 149, data is all collectively registered for each doctor, including basic information such as doctor's name, the probing questionnaire result, the closing questionnaire result, and the answer for the MR contact request.

Therefore, access is made from the pharmaceutical company's management department terminal 13 and the MR terminal 12 to the medical information providing server 100 for browsing the reference doctor specific file 149, and thus information in the medical market can be grasped at individual doctor level.

More specifically, sine detailed market information can be obtained, pharmaceutical companies can facilitate to configure sales strategies.

Furthermore, the MR browses the reference doctor specific file 149 of the doctor in his/her charge, and thus the MR can easily, promptly knows whether the doctor in his/her charge would like to make contact with the MR for allowing efficient activities.

Then, the MR daily report creating program 151 creates MR daily report data as shown in FIG. 12 (ST40). The MR uses this MR daily report data, and the MR can use it as daily reports for visiting doctors. Thus, daily reports can be created easily, quickly.

Moreover, by sending MR daily report data to his/her company, the MR sends the reference doctor specific file 149 inputted with doctor visit information to the company. Therefore, the descriptions of the MR daily reports are improved.

In addition, the pharmaceutical company that received the daily report like this can obtain detailed information about doctors as well as the daily visit report, and thus it can accurately grasp circumstances.

Program and computer readable recording medium

A control program can be configured for a medical information providing apparatus, the program allows a computer to implement the exemplary operation described above: the individual doctor information storing step, the access information creating and input step, the medical information program selecting step, the program guide information creating and sending step, the doctor specifying step, the basic questionnaire information providing step, the program providing order selecting step, program providing step, the basic questionnaire answer information input step, final questionnaire information providing step, the final questionnaire answer information input step, the contact request questionnaire information specifying step, the contact request questionnaire information providing step, the contact request questionnaire answer input step, and the reference individual doctor information creating and input step.

In addition, a computer readable recording medium can be configured on which the control program of the medical information providing apparatus like this is recorded.

For a program storage medium which is used to install the control program of the medical information providing apparatus in the computer and allows the computer to implement it, it can be implemented by package media including a flexible disk such as floppy (trademark), CD-ROM (Compact Disc Read Only Memory), CD-R (Compact Disc-Recordable), CD-RW (Compact Disc-Rewritable), DVD (Digital Versatile Disc) as well as semiconductor memory, a magnetic disk, or a magneto-optical disk on which the program is stored temporarily or permanently.

While there has been described what are at present considered to be beneficial and exemplary embodiments of the invention, it will be understood that various modifications may be made thereto, and it is intended that the appended claims cover all such modifications as fall within the true spirit and scope of the invention. The invention is not limited to the embodiments described above.

What is claimed is:

1. A medical information providing apparatus which is arranged to be able to communicate with a doctor side terminal manipulated by a doctor and a representative side terminal manipulated by a medical information representative who provides medical information to the doctor, the medical information providing apparatus comprising:

an individual doctor information storing module configured to store doctor specific information including communication address information about the doctor side terminal specific to a doctor, doctor specialization information, and representative information, wherein the doctor specific information is inputted from the representative side terminal on a doctor specific file;

an access information creating and input program configured to add identification information varied for each doctor to a URL that permits the doctor side terminal to access the medical information providing apparatus, create the URL containing identification information, and enter the URL containing identification information to the doctor specific file;

a medical information selecting program configured to select pharmaceutical viewable programs specific to the orientation of the doctor from among a plurality of pharmaceutical information viewable programs of a viewable program information file which are classified by a clinical departments and stored;

a guide information viewable program creating and sending program configured to create viewable programs providing guide information, including: an email sent to an email address of the doctor side terminal, the email including a URL having the information about the viewable program selected by the medical information selecting program and wherein the guide information viewable program creating and sending program is configured such that when the doctor who has received the e-mail sent by the guide information viewable program creating and sending program clicks the URL via the doctor side terminal, the information is sent to the medical information providing apparatus;

a doctor specifying program configured to specify the doctor specific file of the doctor from the identification information added to the URL;

a representative presence or absence determining program configured to refer to a column of a medical information representative in charge of the doctor specific file, determine whether the medical information representative in charge is registered, determine when any medical information representative is not registered, refer to a hospital and a list table, and determine the medical information representative in charge;

a probing questionnaire providing program configured to provide a probing questionnaire including the number of patients, recognition medicines, medicine use circumstances, and the number of patients of specific diseases in the probing questionnaire file to the doctor terminal;

a viewable program providing order selecting program configured to select a viewable program providing order based on answers of the probing questionnaire, including the number of patients, recognition medicines, medicine use circumstances, and the number of patients of specific diseases in the probing questionnaire file to the doctor terminal, which are sent back from the doctor and a viewable program providing order file which stores multiple items of viewable program providing order information that decide the order of providing multiple viewable contents based on the prescribed doctor's orientation;

the viewable program providing program configured to distribute the viewable program in the selected viewable program providing order to the doctor side terminal and wherein, when the doctor finishes viewing the viewable program, a viewing rejected viewable program input program is configured to determine whether there is viewable contents that the doctor has not viewed, when there is a no-viewed contents and list the contents in a column of viewing rejected viewable programs in the doctor specific file;

a probing questionnaire answer information input program configured to register the answer for the probing questionnaire on the doctor specific file referring to the medicine use circumstances answered in the probing questionnaire, and determine whether the medicine has been prescribed;

a closing questionnaire providing program configured to select a closing questionnaire from a closing questionnaire file which stores the closing questionnaire for aiding in understanding a change in orientation of a doctor's prescription after viewing the viewable contents about medicine in accordance with information of whether the doctor has used or not used the medicine in answer to the probing questionnaire, and provide it to the doctor side terminal, and wherein when a reply for the closing questionnaire is received from the doctor side terminal, a closing questionnaire answer information input program is configured to enters the result in the doctor specific file;

a medical representative contact request questionnaire specifying program configured to specify a pattern from the contact request questionnaire about making contact with a doctor concerning a medicine based on the information from the doctor specific file, including answers for the probing questionnaire and the closing questionnaire; and a reference doctor specific file creating program configured to create reference individual doctor information for a pharmaceutical company and a medical information representative, based on the information from the doctor specific file, and enter it to a reference doctor specific file.

2. The medical information providing apparatus according to claim 1 comprising:

an overlap registration determination notifying module which determines whether the doctor specific information inputted from the representative side terminal already exists in the doctor specific file, and notifies the representative side terminal that the doctor specific information has been already registered when it exists.

3. The medical information providing apparatus according to claim 1 comprising:

a communication address information appropriateness determination input module which determines whether the address information is appropriate based on a communication result communicated in accordance with communication address information in the doctor side terminal, and enters the address information to the doctor specific file; and a communication address incorrect information notifying module which notifies the representative side terminal of the communication address information being registered as incorrect on the doctor specific file.

4. The medical information providing apparatus according to claim 1 comprising:

a disclosure propriety verification information sending module which sends to the doctor side terminal verification information about propriety of disclosure of the viewing rejected viewable program information, the answer for the probing questionnaire information, and an answer for the closing questionnaire information for the pharmaceutical company and medical information representative; and a disclosure propriety verification information input module which enters verification information about propriety of the disclosure from the doctor side terminal to the doctor specific file, wherein as for the doctor specific file on which appropriateness of the disclosure is registered as negative, the reference doctor specific file creating program changes the viewing rejected viewable program information, the answer to the probing questionnaire, and the answer for the closing questionnaire to non-disclosure status, and creates the reference doctor specific file.

5. The medical information providing apparatus according to claim 1 comprising:

a medical information representative daily report creating module which adds doctor visit information about the medical information representative in charge of a relevant doctor to the reference doctor specific file, and forms it into medical information representative daily report information.

6. The medical information providing apparatus according to claim 2 comprising:

a communication address information appropriateness determination input module which determines whether the address information is appropriate based on a communication result communicated in accordance with communication address information in the doctor side terminal, and enters the address information in the doctor specific file; and a communication address incorrect information notifying module which notifies the representative side terminal of the communication address information being registered as incorrect on the doctor specific file.

7. The medical information providing apparatus according to claim 2 comprising:

a medical information representative daily report creating module which adds doctor visit information about the medical information representative in charge of a relevant doctor to the reference doctor specific file, and forms it into medical information representative daily report information.

8. The medical information providing apparatus according to claim 3 comprising:

a medical information representative daily report creating module which adds doctor visit information about the medical information representative in charge of a relevant doctor to the reference doctor specific file, and forms it into medical information representative daily report information.

9. A medical information providing method which is arranged to be able to communicate with a doctor side terminal manipulated by a doctor and a representative side terminal manipulated by a medical information representative who provides medical information to the doctor, the medical information providing method comprising:

storing doctor specific information including communication address information about the doctor side terminal specific to a doctor, doctor specialization information, and representative information, the doctor specific information being inputted from the representative side terminal on a doctor specific file;

creating and inputting access information wherein the access information creating and input program adds identification information varied for each doctor to a URL that permits the doctor side terminal to access a medical information providing apparatus, creates the URL containing identification information, and enters the URL containing identification information to the doctor specific file;

selecting medical information wherein a medical information selecting program selects pharmaceutical viewable programs specific to the orientation of the doctor from among pharmaceutical information viewable programs of a viewable program information file which are classified by clinical department and stored;

creating and sending viewable program guide information wherein the viewable program guide information creating and sending program creates viewable program providing guide information with an email added to a URL having identification information about the viewable program selected by the medical information selecting program, the email being sent to the email address of the doctor side terminal, and when the doctor who has received an email sent by the viewable program guide information creating and sending program clicks the URL by the doctor side terminal and the information is sent to the medical information providing apparatus;

specifying a doctor specific file wherein the doctor specifying program specifies the doctor specific file of the doctor from the identification information add to the URL;

providing a representative presence or absence determining program which refers to a column of a medical information representative in charge in the doctor specific file, determines whether the medical information representative in charge is registered, when any medical information representative is not registered, the representative specifying program refers to the hospital and list table, and specifies the medical information representative in charge;

providing a probing questionnaire providing program which provides a probing questionnaire including the number of patients, recognition medicines, medicine use circumstances, and the number of patients of specific diseases in the probing questionnaire file to the doctor terminal;

providing a viewable program providing order selecting program which selects a viewable program providing order based on the answers to the probing questionnaire, including the number of patients, recognition medicines, medicine use circumstances, and the number of patients of specific diseases in the probing questionnaire file to the doctor terminal, which are sent back from the doctor and the viewable program providing order file which stores multiple items of viewable program providing order information that decide the order of providing multiple viewable contents based on a prescribed doctor's orientation, wherein the viewable program providing program distributes the viewable program in the selected viewable program providing order to the doctor terminal, and when the doctor finishes viewing the viewable program, the viewing rejected viewable program input program determines whether there are viewable contents that the doctor has not viewed, when there is a no-viewed contents and the contents are listed in a column of viewing rejected viewable program in the doctor specific file;

providing a probing questionnaire answer information input program which registers the answer for the probing questionnaire on the doctor specific file;

referring to the medicine use circumstances result in the probing questionnaire, and determining whether the medicine has been prescribed;

providing a closing questionnaire providing program which selects a closing questionnaire from a closing questionnaire file which stores the closing questionnaire for grasping change in orientation on doctor's prescription after viewing the viewable contents about medicine in accordance with information of whether the doctor has used or not used the medicine in the probing questionnaire, and provides it to the doctor side terminal and when a reply for the closing questionnaire is received from the doctor side terminal, a closing questionnaire answer information input program enters the result in the doctor specific file;

providing a medical representative contact request questionnaire specifying program which specifies a pattern from a medical representative contact request questionnaire about a medical representative making contact with the doctor concerning a medicine based on the information in the doctor specific file, including answers for the probing questionnaire and the closing questionnaire; and providing a reference doctor specific file creating program which creates a reference individual doctor information for a pharmaceutical company and a medical information representative based on the information in the doctor specific file and enters it to a reference doctor specific file.

10. A computer readable recording medium recorded with medical information providing method which is arranged to be able to communicate with a doctor side terminal manipulated by a doctor and a representative side terminal manipulated by a medical information representative who provides medical information to the doctor, the medical information providing method comprising:

storing doctor specific information including communication address information about the doctor side terminal specific to a doctor, doctor specialization information, and representative information, the doctor specific information being inputted from the representative side terminal in a doctor specific file;

creating and inputting access information, wherein an access information creating and input program adds identification information varied for each doctor to a URL that permits the doctor side terminal to have access to a medical information providing apparatus, creates the URL containing identification information, and enters the URL containing identification information to the doctor specific file;

selecting pharmaceutical viewable programs wherein a medical information selecting program selects pharmaceutical viewable programs specific to the orientation of the doctor among pharmaceutical information viewable programs of a viewable program information file which are classified by clinical department and stored;

creating and sending viewable program guide information, wherein a viewable program guide information creating and sending program creates viewable program providing guide information with an email added with to a URL having identification information about the viewable program selected by the medical information selecting program, the email having the viewable program providing guide information which is sent to the email address of the doctor side terminal;

clicking the URL via the doctor side terminal when the doctor who has received the email sent by the viewable program guide information creating and sending program and the viewable program guide information is sent to the medical information providing apparatus, wherein a doctor specifying program specifies the doctor specific file of the doctor from the identification information added to the URL;

providing a representative presence or absence determining program which refers to a column of a medical information representative in charge of the doctor specific file, determines whether the medical information representative in charge is registered and when any medical information representative is not registered, the representative specifying program refers to a hospital and list table, and specifies the medical information representative in charge;

providing a probing questionnaire providing program which provides a probing questionnaire including the number of patients, recognition medicines, medicine use circumstances, and the number of patients of specific diseases in the probing questionnaire file to the doctor terminal;

providing a viewable program providing order selecting program which selects a viewable program providing order based on the answer for the probing questionnaire, including the number of patients, recognition medicines, medicine use circumstances, and the number of patients of specific diseases in the probing questionnaire file to the doctor terminal, which are sent back from the doctor and a viewable program providing order file which stores multiple items of viewable program providing order information that decide the order of providing multiple viewable contents based on the prescribed doctor's orientation, wherein the viewable program providing program distributes the viewable program in the selected viewable program providing order to the doctor side terminal and when the doctor finishes viewing the viewable program, a viewing rejected viewable program input program determines whether there is viewable contents that the doctor has not viewed and when there is a no-viewed contents, the contents are listed in a column of viewing rejected viewable program in the doctor specific file;

providing a probing questionnaire answer information input program which registers the answer for the probing questionnaire in the doctor specific file;

referring to a medicine use circumstances result in the probing questionnaire, and determined whether a medicine has been prescribed;

providing a closing questionnaire providing program which selects a closing questionnaire from a closing questionnaire file which stores the closing questionnaire for grasping change in orientation of a doctor's prescription after viewing the viewable contents about medicine in accordance with information of whether the doctor has used or not used the medicine in the probing questionnaire, provides it to the doctor side terminal and when a reply for the closing questionnaire is received from the doctor side terminal, the closing questionnaire answer information input program enters the result in the doctor specific file;

providing a medical representative contact request questionnaire specifying program which specifies a pattern of the medical representative contact request questionnaire about a medical representative making contact with a doctor concerning a medicine based on the information of the doctor specific file including answers for the probing questionnaire and the closing questionnaire; and providing a reference doctor specific file creating program which creates a reference individual doctor information for a pharmaceutical company and a medical information representative based on the information in the doctor specific file and enters it to a reference doctor specific file.

* * * * *